(12) United States Patent
Grompe et al.

(10) Patent No.: US 8,569,573 B2
(45) Date of Patent: Oct. 29, 2013

(54) METHOD OF EXPANDING HUMAN HEPATOCYTES IN VIVO

(75) Inventors: Markus Grompe, Portland, OR (US); Hisaya Azuma, Tokyo (JP); Muhsen Al-Dhalimy, Beaverton, OR (US); Mark A. Kay, Los Altos, CA (US)

(73) Assignees: Oregon Health & Science University, Portland, OR (US); The Board of Trustees of the Leland Stanford Junior University, Palo Alto, CA (US)

( * ) Notice: Subject to any disclaimer, the term of this patent is extended or adjusted under 35 U.S.C. 154(b) by 699 days.

(21) Appl. No.: 12/663,219

(22) PCT Filed: Jun. 5, 2008

(86) PCT No.: PCT/US2008/065937
§ 371 (c)(1),
(2), (4) Date: Apr. 15, 2010

(87) PCT Pub. No.: WO2008/151283
PCT Pub. Date: Dec. 11, 2008

(65) Prior Publication Data
US 2010/0325747 A1    Dec. 23, 2010

Related U.S. Application Data

(60) Provisional application No. 60/933,432, filed on Jun. 5, 2007.

(51) Int. Cl.
*A01K 67/027* (2006.01)
*C12N 5/071* (2010.01)

(52) U.S. Cl.
USPC .......................... 800/18; 424/93.7; 435/370

(58) Field of Classification Search
USPC .......................... 800/18; 424/93.7; 435/370
See application file for complete search history.

(56) References Cited

U.S. PATENT DOCUMENTS

| | | | |
|---|---|---|---|
| 5,912,173 A | 6/1999 | Leonard | |
| 5,980,886 A | 11/1999 | Kay et al. | |
| 6,509,514 B1 | 1/2003 | Kneteman et al. | |
| 2005/0255591 A1 | 11/2005 | Mukaidani et al. | |

FOREIGN PATENT DOCUMENTS

| | | |
|---|---|---|
| EP | 1496110 A1 | 1/2005 |
| EP | 1 496 110 | * 12/2005 |
| WO | 00/17338 | 3/2000 |
| WO | 01/67854 | 9/2001 |

OTHER PUBLICATIONS

Aponte et al. (2001) PNAS, vol. 98(2), 641-645.*
Grompe et al. (1993) Genes and Develop., vol. 7, 2298-2307.*
Traggiai et al. (2004) Science, vol. 304(5667), 104-107.*
Shafritz et al. (2007) Nat. Biotech., vol. 25(8), 871-872.*
Azuma et al. (2007) Nat. Biotech., vol. 25(8), 903-910.*
Turrini et al. (2006) Transplant. Proc., vol. 38, 1181-1184.*
Chen et al., "Identification of a Key Pathway Required for the Sterile Inflammatory Response Triggered by Dying Cells," *Nat. Med.*, 13(7):851-856 (2007).
Overturf et al., "Serial Transplantation Reveals the Stem-Cell-Like Regenerative Potential of Adult Mouse Hepatocytes," *Am. J. Pathol*, 151(5):1273-1280 (1997).
Barth et al., "Mouse Models for the Study of HCV Infection and Virus-Host Interactions," *J. Hepatol.*, 49:134-142 (2008).
Aponte et al., "Point mutations in the murine fumarylacetoacetate hydrolase gene: Animal models for the human genetic disorder hereditary tyrosinemia type 1," *PNAS USA* 98(2):641-645, Jan. 2001.
Azuma et al., "Robust expansion of human hepatocytes in $Fah^{-/-}/Rag2^{-/-}/Il2rg^{-/-}$ mice," *Nature Biotechnology* 25(8):903-910, Jul. 2007.
Bissig et al., "Repopulation of adult and neonatal mice with human hepatocytes: A chimeric animal model," *PNAS USA* 104(51):20507-20511, Dec. 2007.
Dandri et al., "Repopulation of mouse liver with human hepatocytes and in vivo infection with hepatitis B virus," *Hepatology* 33(4):981-988, Apr. 2001.
Endo & Sun, "Tyrosinaemia type I and apoptosis of hepatocytes and renal tubular cells," *J. Inherit. Metab. Dis.* 25(3):227-234, May 2002.
Grompe et al., "Loss of fumarylacetoacetate hydrolase is responsible for the neonatal hepatic dysfunction phenotype of lethal albino mice," *Genes and Development* 7:2298-2307, Sep. 1993.
Katoh et al., "Expression of human cytochromes P450 in chimeric mice with humanized liver," *American Society for Pharmacology and Experimental Therapeutics* 32(12):1402-1410, Sep. 2004.
Katoh et al., "In vivo induction of human cytochrome P450 enzymes expressed in chimeric mice with humanized liver," *American Society for Pharmacology and Experimental Therapeutics* 33(6):754-763, Mar. 2005.
Katoh et al., "Chimeric mice with humanized liver," *Toxicology* 246(1):9-17, Nov. 2007.
Klebig et al., "Murine fumarylacetoacetate hydrolase (*Fah*) gene is disrupted by a neonatally lethal albino deletion that defines the hepatocyte-specific developmental regulation 1 (*hsdr-1*) locus," *PNAS USA* 89(4):1363-1367, Feb. 1992.
Mercer et al., "Hepatitis C virus replication in mice with chimeric human livers," Nature Medicine 7(8):927-933, Aug. 2001.
Nakamura et al., "Animal models of tyrosinemia," *J. Nutrition* 137(6sup1):1556S-1560S, Jun. 2007.
O'Brien et al., "Murine retroviral restriction genes *Fv-4* and *Akvr-1* are alleles of a single locus," *J. Virology* 47(3):649-651, Sep. 1983.
Overturf et al., "The repopulation potential of hepatocyte populations differing in size and prior mitotic expansion," *AM. J. Pathol.* 155(6):2135-2143, Dec. 1999.

(Continued)

Primary Examiner — Anne Marie S Wehbe
(74) Attorney, Agent, or Firm — Hovey Williams LLP

(57) ABSTRACT

Described herein is a method of expanding human hepatocytes in vivo using an immunodeficient mouse which is further deficient in fumarylacetoacetate hydrolase (Fah). The method comprises transplanting human hepatocytes into the immunodeficient and Fah-deficient mice, allowing the hepatocytes to expand and collecting the expanded human hepatocytes. The method also allows serial transplantation of the human hepatocytes into secondary, tertiary, quaternary or additional mice. Also provided are mutant mice comprising homozygous deletions or point mutations in the Fah, Rag2 and Il2rg genes.

27 Claims, 17 Drawing Sheets

(56) References Cited

OTHER PUBLICATIONS

Shafritz, "A human hepatocyte factory," *Nature Biotechnology* 25:871-872, Aug. 2007.

Shultz et al., "Humanized mice in translational biomedical research," *Nat. Rev. Immunol.* 7(2):118-130, Feb. 2007.

Tateno et al., "Near completely humanized liver in mice shows human-type metabolic responses to drugs," *Am. J. Pathol.* 165(3):901-912, Sep. 2004.

Traggiai et al., "Development of a human adaptive immune system in cord blood cell-transplanted mice," *Science* 304(5667):104-107, Apr. 2004.

Turrini et al., "Development of humanized mice for the study of hepatitis C virus infection," *Transplant Proc.* 38(4):1181-1184, May 2006.

Wang et al., "The origin and liver repopulating capacity of murine oval cells," *PNAS USA* 100(1):11881-11888, Sep. 2003.

Willenbring et al., "Myelomonocytic cells are sufficient for therapeutic cell fusion in liver," Nature Medicine 10(7):744-748, Jul. 2004.

International Search Report from PCT/US2008/065937, dated Aug. 22, 2008.

Written Opinion of the International Searching Authority from PCT/US2008/065937.

Al-Dhalimy et al., "Long-term therapy with NTBC and tyrosine-restricted diet in a murine model of hereditary tyrosinemia type I," *Mol Genet Metab* 75(1):38-45, 2002.

Bissig et al., "Human liver chimeric mice provide a model for hepatitis B and C virus infection and treatment," *J Clin Invest* 120(3):924-930, 2010.

van Rijn et al., "A new xenograft model for graft-versus-host disease by intravenous transfer of human peripheral blood mononuclear cells in RAG2 $4^{-/-}$ $\gamma c^{-/-}$ double-mutant mice," *Blood* 102(7):2522-2531, 2003.

Yoshitsugu et al., "Evaluation of human CYP1A2 and CYP3A4 mRNA expression in hepatocytes from chimeric mice with humanized liver," *Drug Metab Pharmacokinet* 21(6):465-474, 2006.

\* cited by examiner

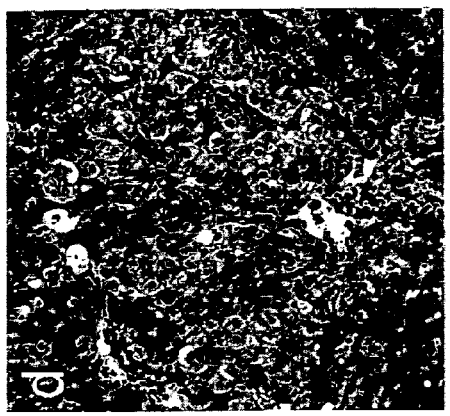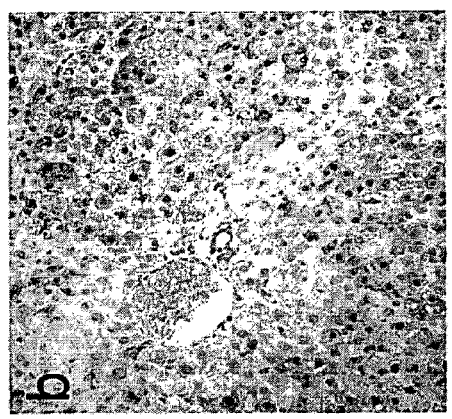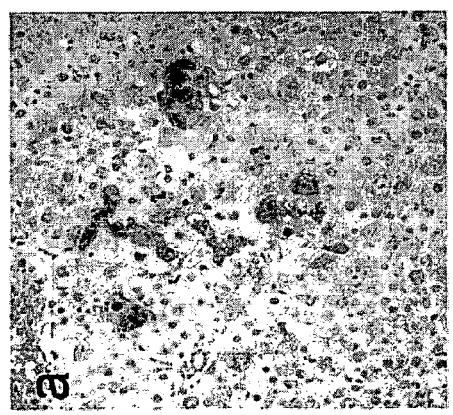

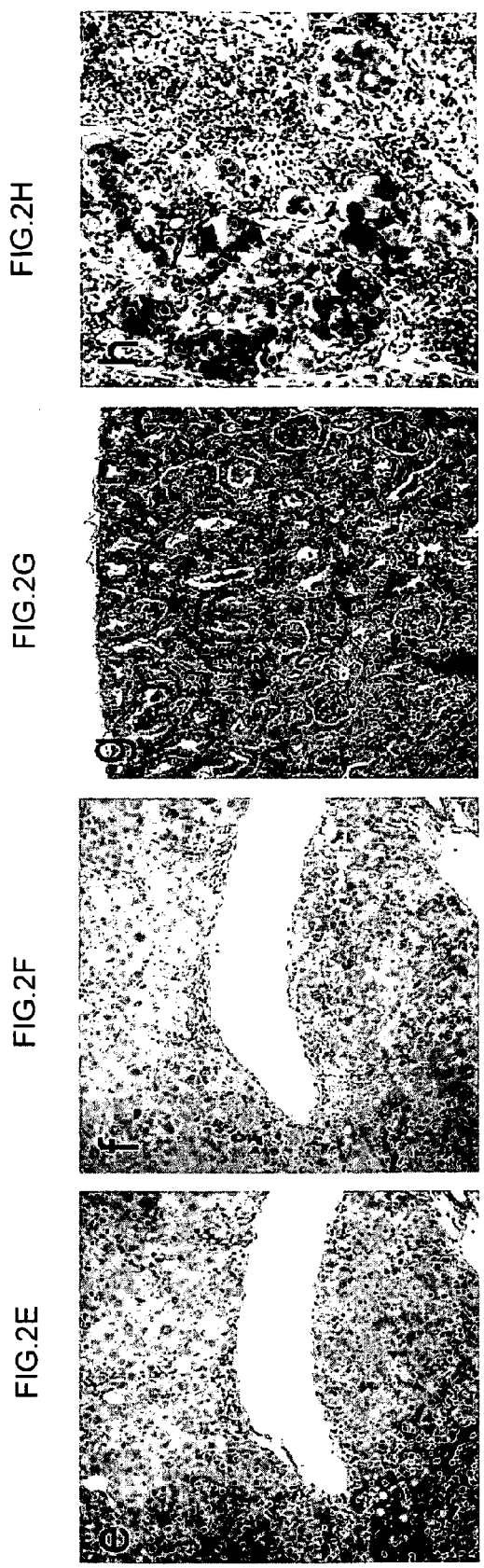

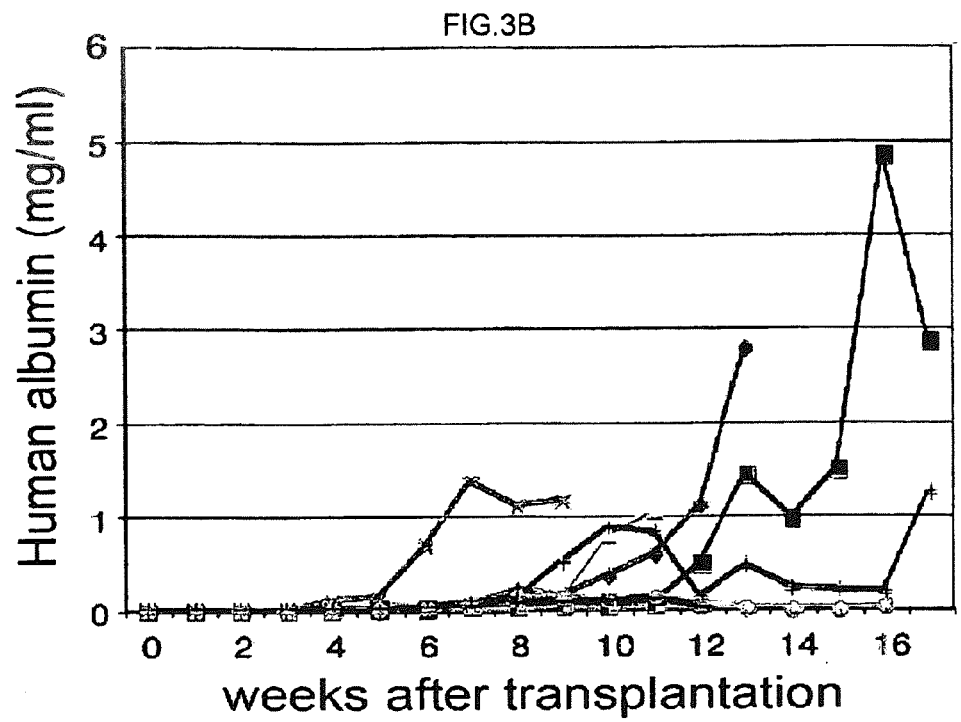
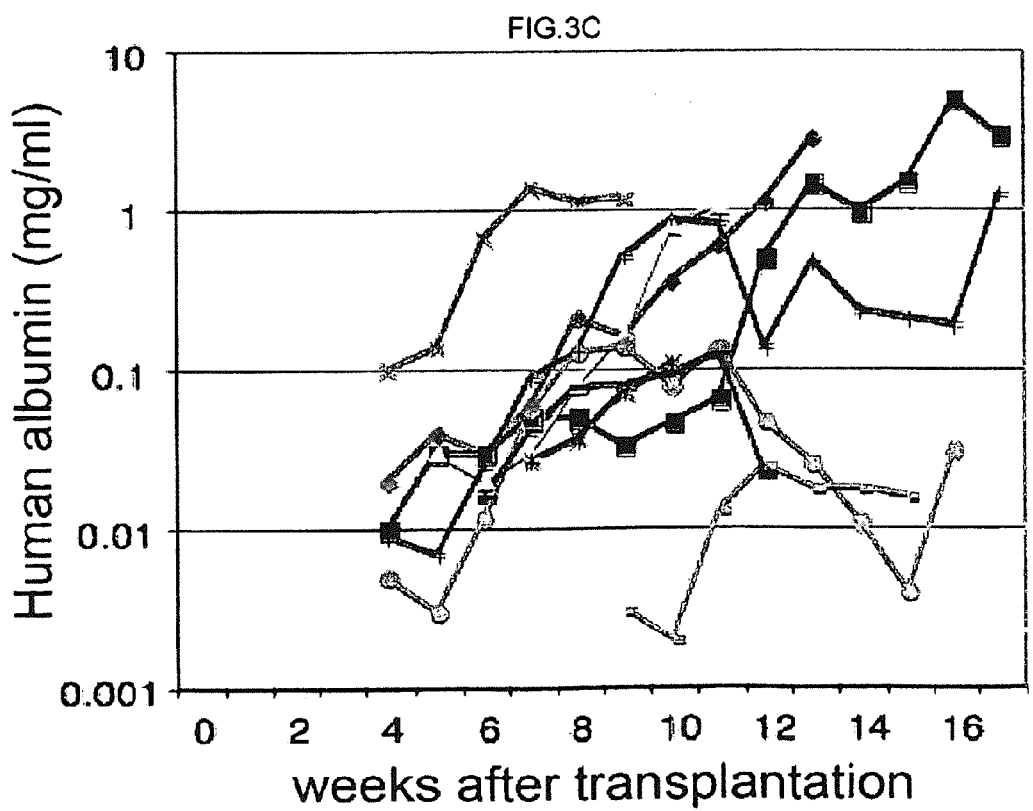

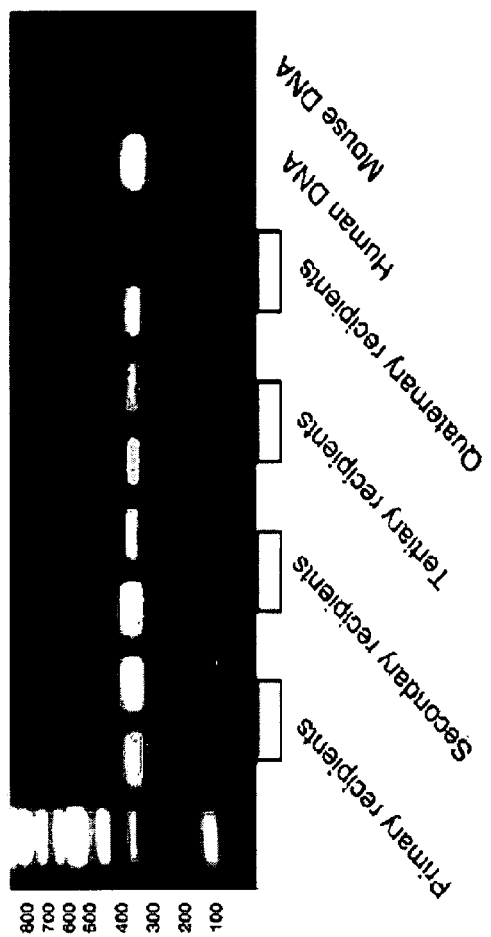
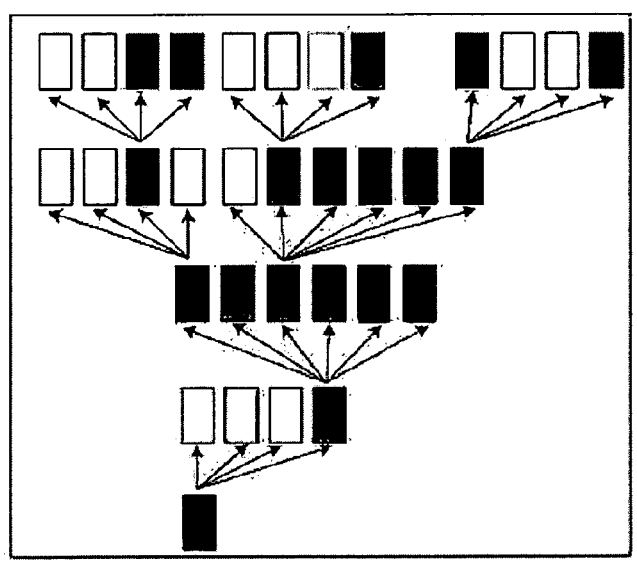
FIG. 4B
FIG. 4A

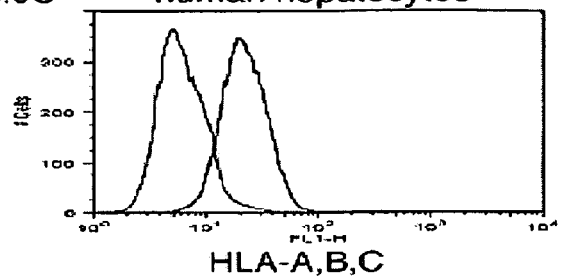
FIG.5G human hepatocytes — HLA-A,B,C
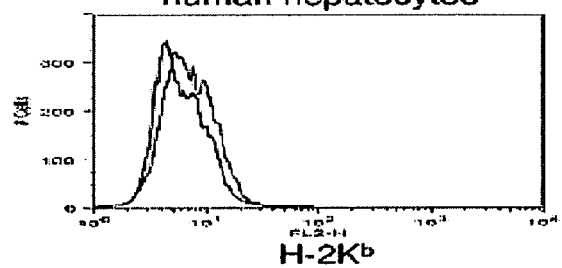
FIG.5H human hepatocytes — H-2K$^b$
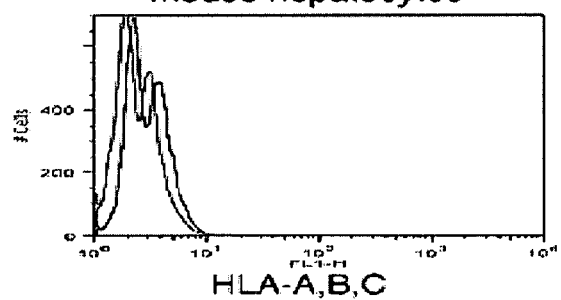
FIG.5I mouse hepatocytes — HLA-A,B,C
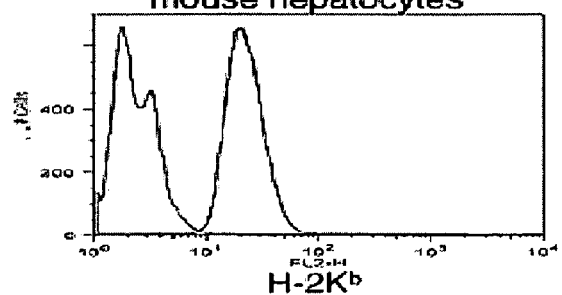
FIG.5J mouse hepatocytes — H-2K$^b$

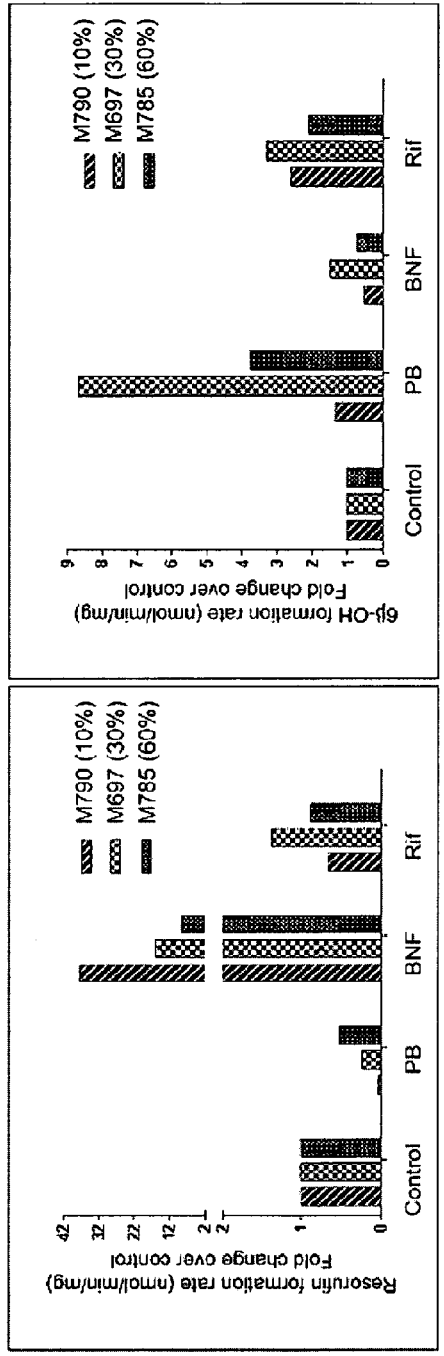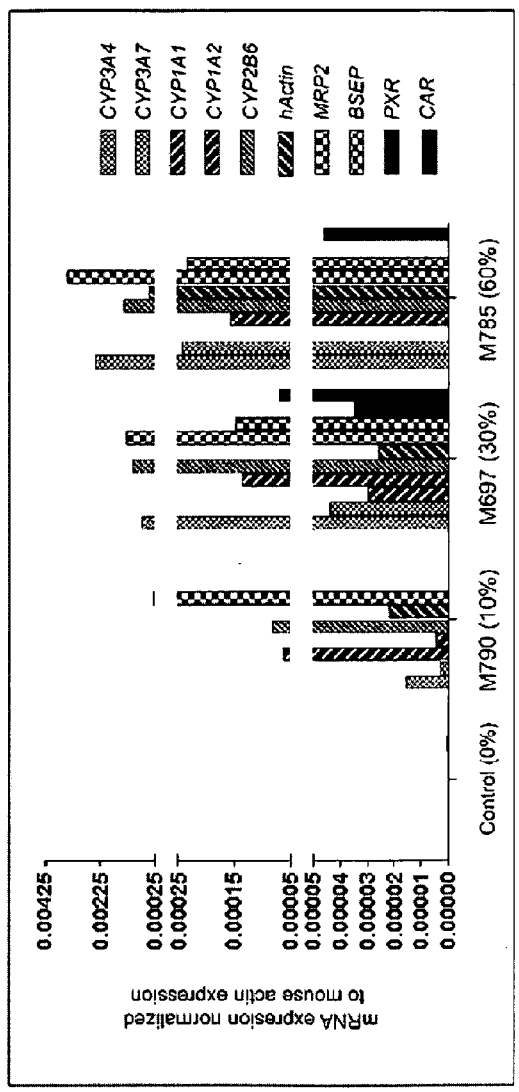

SEQUENCE LISTING

<160> NUMBER OF SEQ ID NOS: 16

<210> SEQ ID NO 1
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1
ggcgcggtgg ctcacg                                          16

<210> SEQ ID NO 2
<211> LENGTH: 23
<212> TYPE: DNA

```
<213> ORGANISM: Artificial sequence
<220> FEATURE:
<223> OTHER INFORMATION: Synthetic oligonucleotide

<400> SEQUENCE: 2 tttttttgaga cggagtctcg ctc                                           23

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
atggatgatt tcgcagcttt                                                20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tggctttaca ccaacgaaaa                                                20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
tacagcggag caactgaaga                                                20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
ttgcagcaca gagacaagaa                                                20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ccgggagagt tttaccacaa                                                20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ccttccctag atgggacaca                                                20
```

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctgacctcac ctgggacaat                                            20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
cctccacagg tttcctggta                                            20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tttgggacca ctgtctctcc                                            20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ctgaccattc cccaggtcta                                            20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
atggcttctc atcgtctgct                                            20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
gctcctcatt ccttgggatt                                            20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 15
gtgcctttat cacccatgct                                                   20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tcttggattt gtgggctttc                                                   20
```

METHOD OF EXPANDING HUMAN HEPATOCYTES IN VIVO

CROSS REFERENCE TO RELATED APPLICATIONS

This application is the U.S. National Stage of International Application No. PCT/US2008/065937, filed Jun. 5, 2008, which was published in English under PCT Article 21(2), which in turn claims the benefit of priority of U.S. provisional application No. 60/933,432, filed Jun. 5, 2007, which is herein incorporated by reference in its entirety.

STATEMENT OF GOVERNMENT SUPPORT

This invention was made with United States government support under grant DK051592, from the National Institute of Diabetes and Digestive and Kidney Diseases of the National Institutes of Health. The United States government has certain rights in the invention.

FIELD

This disclosure is directed to a method for expanding human hepatocytes, specifically to methods that utilize immunodeficient mice to expand human hepatocytes.

BACKGROUND

The liver is the principal site for the metabolism of xenobiotic compounds including medical drugs. Because many hepatic enzymes are species-specific, it is necessary to evaluate the metabolism of candidate pharmaceuticals using cultured primary human hepatocytes or their microsomal fraction (Brandon et al. *Toxicol. Appl. Pharmacol.* 189:233-246, 2003; Gomez-Lechon et al. *Curr. Drug Metab.* 4:292-312, 2003). While microsomal hepatocyte fractions can be used to elucidate some metabolic functions, other tests depend on living hepatocytes. Some compounds, for example, induce hepatic enzymes and thus their metabolism changes with time. To analyze enzyme induction, hepatocytes must be not only viable, but fully differentiated and functional.

For drug metabolism and other studies, hepatocytes are typically isolated from cadaveric organ donors and shipped to the location where testing will be performed. The condition (viability and state of differentiation) of hepatocytes from cadaveric sources is highly variable and many cell preparations are of marginal quality. The availability of high quality human hepatocytes is further hampered by the fact that they cannot be significantly expanded in tissue culture (Runge et al. *Biochem. Biophys. Res. Commun.* 274:1-3, 2000; Cascio S. M., *Artif. Organs* 25:529-538, 2001). After plating, the cells survive but do not divide. Hepatocytes from readily available mammalian species, such as the mouse, are not suitable for drug testing because they have a different complement of metabolic enzymes and respond differently in induction studies. Immortal human liver cells (hepatomas) or fetal hepatoblasts are also not an adequate replacement for fully differentiated adult cells. Human hepatocytes are also necessary for studies in the field of microbiology. Many human viruses, such as viruses which cause hepatitis, cannot replicate in any other cell type.

Given these limitations, methods of expanding primary human hepatocytes are highly desirable. Thus, provided herein is a robust system for expanding human hepatocytes.

SUMMARY

Provided herein is a method of expanding human hepatocytes in vivo. The method includes injecting isolated human hepatocytes into an immunodeficient mouse, allowing the hepatocytes to expand, and collecting the human hepatocytes.

In several embodiments, human hepatocytes are administered to an immunodeficient recipient mouse, wherein the mouse is further deficient in fumarylacetoacetate hydrolase (Fah). In some embodiments, the mouse is a $Fah^{-/-}/Rag2^{-/-}/Il2rg^{-/-}$ (FRG) mouse. In other embodiments, the mouse is a $Fah^{Pm}/Rag2^{-/-}/Il2rg^{-/-}$ ($F^{Pm}RG$) mouse. In some embodiments of the methods, a vector encoding human urokinase is administered to the mouse prior to injection of the human hepatocytes. In other embodiments, macrophages are depleted from the mouse prior to hepatocyte injection.

In some examples, the human hepatocytes expand in the recipient mouse, such as the FRG mouse or the $F^{Pm}RG$ mouse, for at least about two weeks. The expanded human hepatocytes are collected from the recipient mouse. In one embodiment, the isolated human hepatocytes are injected into the spleen of the recipient mouse, and the expanded human hepatocytes are collected from the liver of the mouse. The collected hepatocytes can be introduced into another recipient mouse, such as an FRG mouse or an $F^{Pm}RG$ mouse, for further expansion. Thus, the method can be used repeatedly for additional expansion of the human hepatocytes.

In one embodiment of the methods provided herein, the Fah-deficient mouse is administered an agent that inhibits, prevents or delays the development of liver disease prior to hepatocyte injection. One such agent is 2-(2-nitro-4-trifluoro-methyl-benzoyl)-1,3 cyclohexanedione (NTBC). NTBC, or other suitable agent, can be administered by any suitable means, including, but limited to, in the drinking water, in the food, or by injection. NTBC is optionally administered for at least about three days to at least about six days following hepatocyte injection.

In several embodiments, human hepatocytes are obtained from an organ donor or from a surgical resection of the liver. In some embodiments, the human hepatocytes are derived from a stem cell. In additional embodiments, human hepatocytes are cryopreserved prior to injection. In further embodiments, the human hepatocytes are from a cell line of hepatocytes.

Also provided herein is a genetically modified mouse whose genome is homozygous for deletions or point mutations in the Fah, Rag2 and Il2rg genes such that the deletions or point mutations result in loss of expression of functional FAH, RAG-2 and IL-2Rγ proteins, wherein the mouse is immunodeficient and exhibits decreased liver function, and wherein human hepatocytes can be expanded in the mouse. In one embodiment, the deletions result in the complete loss of B cells, T cells and NK cells. In another embodiment, the mouse expresses human urokinase.

The foregoing and other features and advantages will become more apparent from the following detailed description of several embodiments, which proceeds with reference to the accompanying figures.

BRIEF DESCRIPTION OF THE FIGURES

FIGS. 2a-h are digital images of histological and immunohistochemical tissue sections from chimeric mice. FIG. 2a is a digital image showing FAH-positive human hepatocytes were integrated in mouse liver tissue and did not disturb recipient liver microstructure. FIG. 2b is a digital image showing that highly repopulated chimeric livers also retained normal structure. FIGS. 2c and 2d are digital images of H&E stains showing human hepatocyte clusters are less eosinophilic. FIG. 2e is a digital image showing serial sections stained for FAH. FIG. 2f is a digital image showing serial sections stained for HepPar. FIG. 2g is a digital image of a kidney section from a highly repopulated mouse showing no tubular or glomerular destruction even 4 months after transplantation. FIG. 2h is a digital image showing FAH positive human hepatocytes in the spleen. Original magnification ×100 (FIG. 2c), ×200 (FIGS. 1a, 2b, 2e, 2f and 2g), ×400 (FIGS. 2d and 2h).

FIG. 4a is a schematic showing the serial transplantation scheme starting with primary cells (dark box at far left). Dark boxes indicate repopulated serial recipients and white boxes indicate non-engrafted mice. Only ¼ of the primary recipients were repopulated but all 6 secondary recipients were engrafted. FIG. 4b is a digital image of a gel showing amplification products of Alu sequence PCR from serially transplanted recipient livers.

FIGS. 5g-l are graphs that show flow cytometric analysis of chimeric mouse hepatocytes. FITC-conjugated anti-HLA A,B,C and PE-conjugated anti-H-2Kb were used. Shown are control human hepatocytes against HLA-A,B,C (FIG. 5g); control mouse hepatocytes against HLA-A,B,C (FIG. 5i); control human hepatocytes against H-2Kb (FIG. 5h); control mouse hepatocytes against H-2Kb (FIG. 5j); and hepatocytes from two highly chimeric mice (FIG. 5k and FIG. 5l), which were singly positive for either HLA or H-2Kb.

FIGS. 6a and 6b are graphs showing metabolism of Ethoxyresorufin-O-deethylase (CYP1A1 dependent) (FIG. 6a) and conversion of testosterone to 6-beta-hydroxyltestosterone (CYP3A4 mediated) (FIG. 6b). Cultured hepatocytes from three mice with different levels of human hepatocyte repopulation (M790 10%; M697 30%; and M785 60%) were analyzed. FIG. 6c is a graph depicting mRNA levels of human specific genes relevant to drug metabolism, transport and conjugation, determined by quantitative RT-PCR. The ratios of human drug metabolism genes are typical of adult human hepatocytes.

FIG. 7a is a bar graph of basal expression of liver-specific genes in the three samples, normalized to mouse actin mRNA. FIGS. 7b-h are bar graphs of induction of mRNAs involved in drug metabolism in response to beta-naphthoflavone (BNF), phenobarbital (PB) and rifampicin (Rif), relative to induction in non-induced cultures. Shown are CYP3A4 (FIG. 7b); CYP2B6 (FIG. 7c); CAR (nuclear hormone receptor) (FIG. 7d); MDR1 (transporter) (FIG. 7e); MRP (FIG. 7f); BSEP (transporter) (FIG. 7g); and PXR (nuclear hormone receptor) (FIG. 7h). The induction of CYP3A4 by phenobarbital was even more striking than at the enzyme level.

SEQUENCE LISTING

Figure 1A:
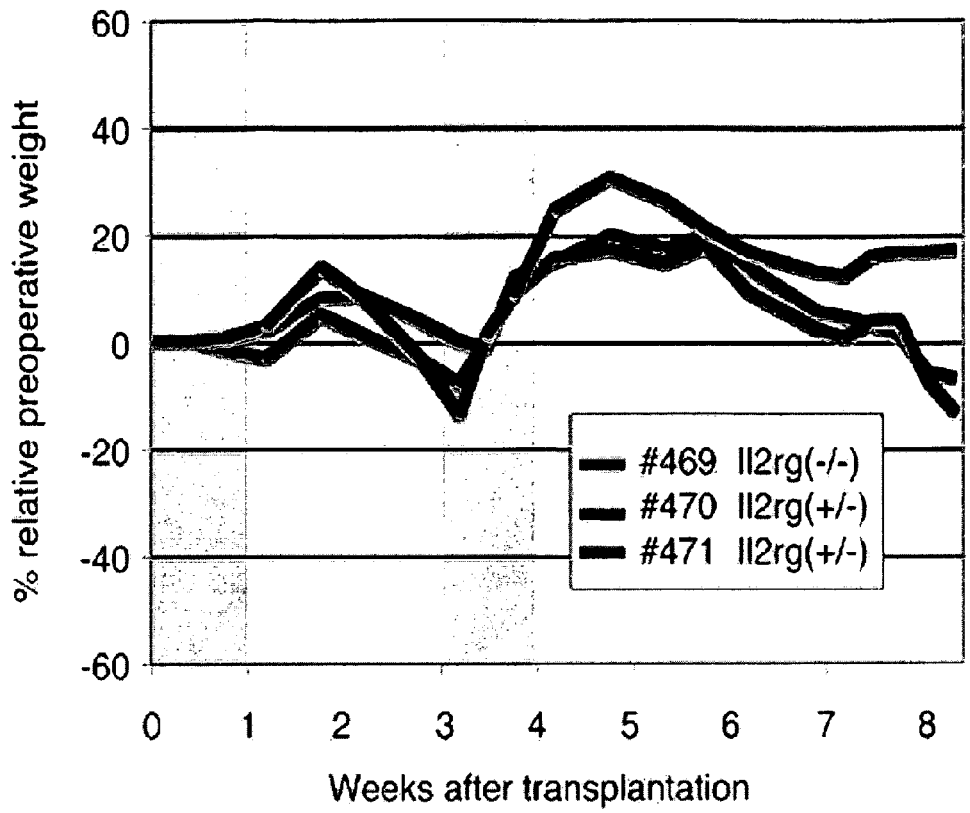
FIG. 1a is a graph showing the relative weight of a triple mutant FRG mouse (#471) and two heterozygote littermates (#469, #470) following engraftment and repopulation by human hepatocytes. The FRG mouse maintained its weight 6 weeks after transplantation; however, the Il2rg gene heterozygote littermates lost weight continuously. NTBC was administered only in the first and the forth week, which is indicated by shading.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 are the nucleic acid sequences of the PCR primers for amplifying human Alu sequences.

SEQ ID NO: 3 is the nucleic acid sequence of the human ALB forward RT-PCR primer.

SEQ ID NO: 4 is the nucleic acid sequence of the human ALB reverse RT-PCR primer.

SEQ ID NO: 5 is the nucleic acid sequence of the mouse Alb forward RT-PCR primer.

SEQ ID NO: 6 is the nucleic acid sequence of the mouse Alb reverse RT-PCR primer.

SEQ ID NO: 7 is the nucleic acid sequence of the human TAT forward RT-PCR primer.

SEQ ID NO: 8 is the nucleic acid sequence of the human TAT reverse RT-PCR primer.

SEQ ID NO: 9 is the nucleic acid sequence of the human TF forward RT-PCR primer.

SEQ ID NO: 10 is the nucleic acid sequence of the human TF reverse RT-PCR primer.

SEQ ID NO: 11 is the nucleic acid sequence of the human FAH forward RT-PCR primer.

SEQ ID NO: 12 is the nucleic acid sequence of the human FAH reverse RT-PCR primer.

SEQ ID NO: 13 is the nucleic acid sequence of the human TTR forward RT-PCR primer.

SEQ ID NO: 14 is the nucleic acid sequence of the human TTR reverse RT-PCR primer.

SEQ ID NO: 15 is the nucleic acid sequence of the human UGT1A1 forward RT-PCR primer.

SEQ ID NO: 16 is the nucleic acid sequence of the human UGT1A1 reverse RT-PCR primer.

DETAILED DESCRIPTION

I. Abbreviations
AAV Adeno-associated virus
ALB Albumin
ALT Alanine aminotransferase
AST Aspartate aminotransferase
BNF Beta-naphthoflavone
DAB Diaminobenzidine
ELISA Enzyme-linked immunosorbent assay
EROD Ethoxyresorufin-O-deethylase
FACS Fluorescence-activated cell sorting
FAH Fumarylacetoacetate hydrolase
FISH Fluorescence in situ hybridization
FITC Fluorescein isothiocyanate
FRG Fah$^{-/-}$/Rag2$^{-/-}$/Il2rg$^{-/-}$ triple mutant mice
HLA Human leukocyte antigen
IL-2Rγ Interleukin-2 receptor gamma
MHC Major histocompatibility complex
NTBC 2-(2-nitro-4-trifluoro-methyl-benzoyl)-1,3 cyclohexanedione
PB Phenobarbital
PBS Phosphate-buffered saline
PCR Polymerase chain reaction
PE Phycoerythrin
PFU Plaque forming units
RAG Recombinase activating gene
Rif Rifampicin
RT-PCR Reverse transcription polymerase chain reaction
TAT Tyrosine aminotransferase
TF Transferrin
TTR Transthyretin
UGT1A1 UDP glucuronosyltransferase 1 family, polypeptide A1
uPA Urokinase plasminogen activator II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Agent that inhibits or prevents the development of liver disease: A compound or composition that when administered to an FRG mouse, an F$^{p'm}$RG mouse, or other type of Fah-deficient mouse, prevents, delays or inhibits the development of liver disease in the mouse. Liver disease or liver dysfunction is characterized by any one of a number of signs or symptoms, including, but not limited to an alteration in liver histology (such as necrosis, inflammation, dysplasia or hepatic cancer), an alteration in levels of liver-specific enzymes and other proteins (such as aspartate aminotransferase, alanine aminotransferase, bilirubin, alkaline phosphatase and albumin) or generalized liver failure. In one embodiment, the agent that inhibits liver disease is 2-(2-nitro-4-trifluoro-methyl-benzoyl)-1,3 cyclohexanedione (NTBC).

Amniocyte: A cell found in the amniotic fluid surrounding an embryo.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

B cell: A type of lymphocyte that plays a large role in the humoral immune response. The principal function of B cells is to make antibodies against soluble antigens. B cells are an essential component of the adaptive immune system.

Collecting: As used herein, "collecting" expanded human hepatocytes refers to the process of removing the expanded hepatocytes from a mouse that has been injected with isolated human hepatocytes (also referred to as a recipient mouse). Collecting optionally includes separating the hepatocytes from other cell types. In one embodiment, the expanded human hepatocytes are collected from the liver of a Fah-deficient mouse. In some examples, the expanded human hepatocytes are collected from the liver of an FRG mouse or an F$^{pm}$RG mouse.

Common-γ chain of the interleukin receptor (Il2rg): A gene encoding the common gamma chain of interleukin receptors. Il2rg is a component of the receptors for a number of interleukins, including IL-2, IL-4, IL-7 and IL-15 (Di Santo et al. *Proc. Natl. Acad. Sci. U.S.A.* 92:377-381, 1995). Animals deficient in Il2rg exhibit a reduction in B cells and T cells and lack natural killer cells.

Cryopreserved: As used herein, "cryopreserved" refers to a cell or tissue that has been preserved or maintained by cooling to low sub-zero temperatures, such as 77 K or −196° C. (the boiling point of liquid nitrogen). At these low temperatures, any biological activity, including the biochemical reactions that would lead to cell death, is effectively stopped.

Decreased liver function: An abnormal change in any one of a number of parameters that measure the health or function of the liver. Decreased liver function is also referred to herein as "liver dysfunction." Liver function can be evaluated by any one of a number of means well known in the art, such as, but not limited to, examination of liver histology and measurement of liver enzymes or other proteins. For example, liver dysfunction can be indicated by necrosis, inflammation, oxidative damage or dysplasia of the liver. In some instances, liver dysfunction is indicated by hepatic cancer, such as hepatocellular carcinoma. Examples of liver enzymes and proteins that can be tested to evaluate liver dysfunction include, but are not limited to, alanine aminotransferase (ALT), aspartate aminotransferase (AST), bilirubin, alkaline phosphatase and albumin. Liver dysfunction also can result in generalized liver failure. Procedures for testing liver function are well known in the art, such as those taught by Grompe et al. (*Genes Dev.* 7:2298-2307, 1993) and Manning et al. (*Proc. Natl. Acad. Sci. U.S.A.* 96:11928-11933, 1999), which are herein incorporated by reference.

Deficient: As used herein, "Fah-deficient" or "deficient in Fah" refers to an animal, such as a mouse, comprising a mutation in Fah, which results in a substantial decrease in, or the absence of, Fah mRNA expression and/or functional FAH protein. In one embodiment, the Fah-deficient animal comprises homozygous deletions in the Fah gene. As one example, the homozygous deletion is in exon 5 of Fah. In another embodiment, the Fah-deficient animal comprises one or more point mutations in the Fah gene. Examples of suitable Fah point mutations are known in the art (see, for example, Aponte et al. *Proc. Natl. Acad. Sci. U.S.A.* 98(2):641-645, 2001, incorporated herein by reference).

Deplete: To reduce or remove. As used herein, "macrophage depletion" refers to the process of eliminating, removing, reducing or killing macrophages in an animal. An animal that has been depleted of macrophages is not necessarily completely devoid of macrophages but at least exhibits a reduction in the number or activity of macrophages. In one embodiment, macrophage depletion results in at least a 10%, at least a 25%, at least a 50%, at least a 75%, at least a 90% or a 100% reduction in functional macrophages.

Engraft: To implant cells or tissues in an animal. As used herein, engraftment of human hepatocytes in a recipient mouse refers to the process of human hepatocytes becoming implanted in the recipient mouse following injection. Engrafted human hepatocytes are capable of expansion in the recipient mouse. As described herein, "significant engraftment" refers to a recipient mouse wherein at least about 1% of the hepatocytes in the liver are human. A "highly engrafted" mouse is one having a liver wherein at least about 30% of the hepatocytes are human. However, engraftment efficiency can be higher, such as at least about 40%, at least about 50%, at least about 60%, at least about 70%, at least about 80%, at least about 90% or at least about 95% of the hepatocytes in the mouse liver are human hepatocytes.

Embryonic stem (ES) cells: Pluripotent cells isolated from the inner cell mass of the developing blastocyst. ES cells are pluripotent cells, meaning that they can generate all of the cells present in the body (bone, muscle, brain cells, etc.). Methods for producing murine ES cells can be found in U.S. Pat. No. 5,670,372, herein incorporated by reference. Methods for producing human ES cells can be found in U.S. Pat. No. 6,090,622, PCT Publication No. WO 00/70021 and PCT Publication No. WO 00/27995, each of which is herein incorporated by reference.

Expand: To increase in quantity. As used herein, "expanding" human hepatocytes refers to the process of allowing cell division to occur such that the number of human hepatocytes increases. As described herein, human hepatocytes are allowed to expand in a recipient mouse for at least about four weeks, at least about six weeks, at least about 8 weeks, at least about 12 weeks, at least about 16 weeks, at least about 20 weeks, at least about 24 weeks or at least about 28 weeks. In one embodiment, the human hepatocytes are allowed to expand for up to about 6 months. The number of human hepatocytes resulting from expansion can vary. In one embodiment, expansion results in at least 10 million, at least 20 million, at least 30 million, at least 40 million or at least 50 million hepatocytes. Assuming one million hepatocytes are initially injected, and approximately 10% engraft, hepatocyte expansion can range from about 10-fold to about 500-fold. In some embodiments, expansion of human hepatocytes in a recipient mouse results in an increase of at least 10-fold, at least 50-fold, at least 100-fold, at least 150-fold, at least 200-fold, at least 250-fold, at least 300-fold, at least 400-fold, at least 500-fold or at least 1000-fold.

FRG mouse: A mutant mouse having homozygous deletions in the fumarylacetoacetate hydrolase (Fah), recombinase activating gene 2 (Rag2) and common-γ chain of the interleukin receptor (Il2rg) genes. Also referred to herein as Fah$^{-/-}$/Rag2$^{-/-}$/Il2rg$^{-/-}$. As used herein, homozygous deletions in the Fah, Rag2 and Il2rg genes indicates no functional FAH, RAG-2 and IL-2Rγ protein is expressed in mice comprising the mutations.

F$^{pm}$RG mouse: A mutant mouse having homozygous deletions in the recombinase activating gene 2 (Rag2) and common-γ chain of the interleukin receptor (Il2rg) genes, and homozygous point mutations in the fumarylacetoacetate hydrolase (Fah). The point mutation in the Fah gene of F$^{pm}$RG mice results in missplicing and loss of exon 7 in the mRNA (Aponte et al., *Proc. Natl. Acad. Sci. USA* 98:641-645, 2001). Also referred to herein as Fah$^{pm}$/Rag2$^{-/-}$Il2rg$^{-/-}$. As used herein, homozygous deletions in the Rag2 and Il2rg genes indicates no functional RAG-2 and IL-2Rγ protein is expressed in mice comprising the mutations. In addition, mice having homozygous point mutations in the Fah gene do not express functional FAH protein.

Fumarylacetoacetate hydrolase (FAH): A metabolic enzyme that catalyzes the last step of tyrosine catabolism. Mice having a homozygous deletion of the Fah gene exhibit altered liver mRNA expression and severe liver dysfunction (Grompe et al. *Genes Dev.* 7:2298-2307, 1993, incorporated herein by reference). Point mutations in the Fah gene have also been shown to cause hepatic failure and postnatal lethality (Aponte et al. *Proc. Natl. Acad. Sci. U.S.A.* 98(2):641-645, 2001, incorporated herein by reference).

Gradually reduced: As used herein, "gradually reducing" the dose of NTBC refers to the process of decreasing the dose of NTBC administered to Fah-deficient mice over time, such as over the course of several days. In one embodiment, the NTBC dose is gradually reduced over about a six day period, wherein the dose is decreased at about one or two day intervals such that after about one week, NTBC is no longer administered. The gradual reduction in NTBC can be performed over a shorter or longer period of time and the intervals of time between decreases in dose can also be shorter or longer.

Hepatocyte: A type of cell that makes up 70-80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile. Hepatocytes manufacture serum albumin, fibrinogen and the prothrombin group of clotting factors and are the main site for the synthesis of lipoproteins, ceruloplasmin, transferrin, complement and glycoproteins. In addition, hepatocytes have the ability to metabolize, detoxify, and inactivate exogenous compounds such as drugs and insecticides, and endogenous compounds such as steroids.

Homozygous: Having identical alleles at one or more loci. As used herein, "homozygous for deletions" refers to an organism have identical deletions of both alleles of a gene.

Immunodeficient: Lacking in at least one essential function of the immune system. As used herein, and "immunodeficient" mouse is one lacking specific components of the immune system or lacking function of specific components of the immune system. In one embodiment, an immunodeficient mouse lacks functional B cells, T cells and/or NK cells. In another embodiment, an immunodeficient mouse further lacks macrophages.

Isolated: An "isolated" hepatocyte refers to a hepatocyte that has been obtained from a particular source, such as an organ donor, and substantially separated or purified away from other cell types.

Macrophage: A cell within the tissues that originates from specific white blood cells called monocytes. Monocytes and macrophages are phagocytes, acting in both nonspecific defense (or innate immunity) as well as specific defense (or cell-mediated immunity) of vertebrate animals. Their role is to phagocytize (engulf and then digest) cellular debris and pathogens either as stationary or mobile cells, and to stimulate lymphocytes and other immune cells to respond to the pathogen.

Natural Killer (NK) cell: A form of cytotoxic lymphocyte which constitute a major component of the innate immune system. NK cells play a major role in the host-rejection of both tumors and virally infected cells.

Recipient: As used herein, a "recipient mouse" is a mouse that has been injected with the isolated human hepatocytes described herein. Typically, a portion (the percentage can vary) of the human hepatocytes engraft in the recipient mouse. In one embodiment, the recipient mouse is an immunodeficient mouse which is further deficient in Fah. In another embodiment, the recipient mouse is a Rag2$^{-/-}$/Il2rg$^{-/-}$ mouse which is further deficient in Fah. In another embodiment, the recipient mouse is an FRG mouse. In another embodiment, the recipient mouse is an F$^{p7m}$RG mouse.

Recombinase activating gene 2 (Rag2): A gene involved in recombination of immunoglobulin and T cell receptor loci. Animals deficient in the Rag2 gene are unable to undergo V(D)J recombination, resulting in a complete loss of functional T cells and B cells (Shinkai et al. *Cell* 68:855-867, 1992).

Serial transplantation: The process for expanding human hepatocytes in vivo in which hepatocytes expanded in a first mouse are collected and transplanted, such as by injection, into a secondary mouse for further expansion. Serial transplantation can further include tertiary, quaternary or additional mice.

Stem cell: A cell having the unique capacity to produce unaltered daughter cells (self-renewal; cell division produces at least one daughter cell that is identical to the parent cell) and to give rise to specialized cell types (potency). Stem cells include, but are not limited to, embryonic stem (ES) cells, embryonic germ (EG) cells, germline stem (GS) cells, human mesenchymal stem cells (hMSCs), adipose tissue-derived stem cells (ADSCs), multipotent adult progenitor cells (MAPCs), multipotent adult germline stem cells (maGSCs) and unrestricted somatic stem cell (USSCs). The role of stem cells in vivo is to replace cells that are destroyed during the normal life of an animal. Generally, stem cells can divide without limit. After division, the stem cell may remain as a stem cell, become a precursor cell, or proceed to terminal differentiation. A precursor cell is a cell that can generate a fully differentiated functional cell of at least one given cell type. Generally, precursor cells can divide. After division, a precursor cell can remain a precursor cell, or may proceed to terminal differentiation. In one embodiment, the stem cells give rise to hepatocytes.

T cell: A type of white blood cell, or lymphocyte, that plays a central role in cell-mediated immunity. T cells are distinguished from other types of lymphocytes, such as B cells and NK cells, by the presence of a special receptor on their cell surface that is called the T cell receptor (TCR). The thymus is generally believed to be the principal organ for T cell development.

Transgene: An exogenous nucleic acid sequence introduced into a cell or the genome of an organism.

Transgenic animal: A non-human animal, usually a mammal, having a non-endogenous (heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, such as, heterologous nucleic acid in the form of an expression construct (such as for the production of a "knock-in" transgenic animal) or a heterologous nucleic acid that upon insertion within or adjacent to a target gene results in a decrease in target gene expression (such as for production of a "knock-out" transgenic animal). A "knock-out" of a gene means an alteration in the sequence of the gene that results in a decrease of function of the target gene, preferably such that target gene expression is undetectable or insignificant. Transgenic knock-out animals can comprise a heterozygous knock-out of a target gene, or a homozygous knock-out of a target gene. "Knock-outs" also include conditional knock-outs, where alteration of the target gene can occur upon, for example, exposure of the animal to a substance that promotes target gene alteration, introduction of an enzyme that promotes recombination at the target gene site (for example, Cre in the Cre-lox system), or other method for directing the target gene alteration postnatally.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes. In one embodiment described herein, the vector comprises a sequence encoding urokinase, such as human urokinase. In one embodiment, the vector is a plasmid vector. In another embodiment, the vector is a viral vector, such as an adenovirus vector or an adeno-associated virus (AAV) vector.

Urokinase: Also called urokinase-type Plasminogen Activator (uPA), urokinase is a serine protease. Urokinase was originally isolated from human urine, but is present in several physiological locations, such as the blood stream and the extracellular matrix. The primary physiological substrate is plasminogen, which is an inactive zymogen form of the serine protease plasmin. Activation of plasmin triggers a proteolytic cascade which, depending on the physiological environment, participates in thrombolysis or extracellular matrix degradation. In one embodiment of the methods provided herein, urokinase is administered to a recipient mouse prior to hepatocyte injection. In some embodiments, urokinase is human urokinase. In some embodiments, the human urokinase is the secreted form of urokinase. In some embodiments, the human urokinase is a modified, non-secreted form of urokinase (see U.S. Pat. No. 5,980,886, herein incorporated by reference).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein is a robust method of expanding human hepatocytes in vivo. The method comprises transplanting isolated human hepatocytes into an immunodeficient mouse that is deficient in the tyrosine catabolic enzyme fumarylacetoacetate hydrolase (Fah). In one embodiment, the immunodeficient mouse is a Rag2$^{-/-}$/Il2rg$^{-/-}$ mouse. In one embodiment, the Fah-deficient mouse comprises a homozygous deletion of Fah. In another embodiment, the Fah-deficient mouse comprises one or more point mutations in Fah, such that the function and/or production of the protein is substantially reduced. As described herein, a triple mutant mice deficient for Fah, recombinase activating gene 2 (Rag2) and the common gamma chain of the interleukin receptor (Il2rg), provide an efficient in vivo system for expanding human hepatocytes in vivo. In some embodiments, the mouse is a Fah$^{-/-}$/Rag2$^{-/-}$/Il2rg$^{-/-}$ (FRG) mouse. In some embodiments, the mouse is a Fah$^{Pm}$/Rag2$^{-/-}$/Il2rg$^{-/-}$ (F$^{Pm}$RG) mouse.

Disclosed herein is a method of expanding human hepatocytes in vivo comprising transplanting isolated human hepatocytes, such as by injection, into an immunodeficient and Fah-deficient mouse (also referred to as a recipient mouse), allowing the human hepatocytes to expand for at least about two weeks and collecting the expanded human hepatocytes from the mouse. The hepatocytes can be transplanted using any suitable means known in the art. In one embodiment, the isolated human hepatocytes are transplanted, such as by injection, into the spleen of the recipient mouse. In another embodiment, the expanded human hepatocytes are collected from the liver of the recipient mouse. The human hepatocytes are allowed to expand in the recipient mouse for a period of time sufficient to permit expansion of the human hepatocytes. The precise period of time for expansion can be determined empirically with routine experimentation. In one embodiment, the human hepatocytes are allowed to expand for up to six months. In another embodiment, the human hepatocytes are allowed to expand for at least about four weeks, at least about six weeks, at least about 8 weeks, at least about 12 weeks, at least about 16 weeks, at least about 20 weeks, at least about 24 weeks or at least about 28 weeks. The extent of hepatocyte expansion can vary. In some embodiments, expansion of human hepatocytes in a recipient mouse results in an increase of at least about 10-fold, at least about 50-fold, at least about 100-fold, at least about 150-fold, at least about 200-fold, at least about 250-fold, at least about 300-fold, at least about 400-fold, at least about 500-fold or at least about 1000-fold.

Also provided is a method of expanding human hepatocytes in vivo wherein a recipient mouse is administered a vector encoding a urokinase gene prior to injection of the human hepatocytes. In one embodiment, the urokinase gene is human urokinase. Wild-type urokinase is a secreted protein. Thus, in some embodiments, the human urokinase is a secreted form of urokinase (Nagai et al., *Gene* 36:183-188, 1985, herein incorporated by reference). Sequences for human urokinase (secreted form) are known in the art, such as, but not limited to the GenBank Accession Nos. AH007073 (deposited Aug. 3, 1993), D11143 (deposited May 9, 1996), A18397 (deposited Jul. 21, 1994), BC002788 (deposited Aug. 19, 2003), X02760 (deposited Apr. 21, 1993), BT007391 (deposited May 13, 2003), NM_002658 (deposited Oct. 1, 2004) and X74039 (deposited Feb. 20, 1994), which are incorporated herein by reference.

In some embodiments, the human urokinase is a modified, non-secreted form of urokinase. For example, Lieber et al. (*Proc. Natl. Acad. Sci.* 92:6210-6214, 1995, herein incorporated by reference) describe non-secreted forms of urokinase generated by inserting a sequence encoding an endoplasmic reticulum retention signal at the carboxyl terminus of urokinase, or by replacing the pre-uPA signal peptide with the amino-terminal RR-retention signal (Strubin et al., *Cell* 47:619-625, 1986; Schutze et al., *EMBO J.* 13:1696-1705, 1994, both of which are incorporated by reference) and the transmembrane anchor separated by a spacer peptide from the membrane II protein Iip33 (Strubin et al., *Cell* 47:619-625, 1986). Non-secreted forms of urokinase are also described in U.S. Pat. No. 5,980,886, herein incorporated by reference.

The vector encoding urokinase can be any type of vector suitable for delivery to a mouse and capable of expressing the urokinase gene. Such vectors include viral vectors or plasmid vectors. In one embodiment, the vector is an adenovirus vector. In another embodiment, the vector is an AAV vector. The vector encoding urokinase can be administered by any suitable means known in the art. In one embodiment, the vector is administered intravenously. In one aspect, the vector is administered by retroorbital injection. The vector encoding urokinase can be administered any time prior to injection of the human hepatocytes. Typically, the vector is administered to allow sufficient time for urokinase to be expressed. In one embodiment, the vector is administered 24 to 48 hours prior to hepatocyte injection.

Further provided herein is a method of expanding human hepatocytes in vivo wherein the recipient mouse is depleted of macrophages prior to injection of the human hepatocytes. In one embodiment, the recipient mouse is administered a vector encoding urokinase prior to macrophage depletion. In another embodiment, the recipient mouse is administered a vector encoding urokinase following macrophage depletion. In another embodiment, the macrophage-depleted recipient mouse is not administered a vector encoding urokinase. Macrophages can be depleted from the recipient mouse using any one of a number of methods well known in the art, such as by using a chemical or an antibody. For example, macrophages can be deleted by administration of an antagonist, such as a toxic substance, including C12MDP, or antibodies altering macrophage development, function and/or viability. The administration of antagonists is performed by well-known techniques, including the use of liposomes, such as described in European Patent No. 1552740, incorporated herein by reference. Clodronate-containing liposomes also can be used to deplete macrophages as described by van Rijn et al. (*Blood* 102:2522-2531, 2003), which is herein incorporated by reference.

In one embodiment of the methods described herein, prior to hepatocyte injection, the Fah-deficient mouse is administered an agent that inhibits, delays or prevents the development of liver disease in the mouse. The agent can be any compound or composition known in the art to inhibit liver disease. On such agent is 2-(2-nitro-4-trifluoro-methyl-benzoyl)-1,3 cyclohexanedione (NTBC). NTBC is administered to regulate the development of liver disease in the Fah-deficient mouse. The dose, dosing schedule and method of administration can be adjusted as needed to prevent liver dysfunction in the Fah-deficient mouse. In one embodiment, the NTBC is administered at a dose of about 0.01 mg/kg/day to about 0.50 mg/kg/day. In another embodiment, the NTBC is administered at a dose of about 0.05 mg/kg/day to about 0.10 mg/kg/day, such as about 0.05 mg/kg/day, about 0.06 mg/kg/day, about 0.07 mg/kg/day, about 0.08 mg/kg/day, about 0.09 mg/kg/day or about 0.10 mg/kg/day. NTBC can be administered prior to injection of human hepatocytes and/or a selected period of time following hepatocyte injection. NTBC can be withdrawn or re-administered as needed during the time of hepatocyte expansion. In one embodiment, the Fah-deficient mouse is administered NTBC prior to hepatocyte injection and for at least about three days following hepatocyte injection. In another embodiment, the Fah-deficient mouse is administered NTBC prior to hepatocyte injection and for at least about six days following hepatocyte injection. In one aspect, the dose of NTBC is gradually reduced over the course of a six day period following hepatocyte injection. NTBC can be administered by any suitable means, such as, but limited to, in the drinking water, in the food or by injection. In one embodiment, the concentration of NTBC administered in the drinking water prior to hepatocyte injection is about 1 to about 8 mg/L, such as about 1 mg/L, about 2 mg/L, about 3 mg/L, about 4 mg/L, about 5 mg/L, about 6 mg/L, about 7 mg/L or about 8 mg/L. In another embodiment, the concentration of NTBC administered in the drinking water prior to hepatocyte injection is about 1 to about 2 mg/L, such as about 1.0 mg/L, about 1.2 mg/L, about 1.4 mg/L, about 1.6 mg/L, about 1.8 mg/L or about 2.0 mg/L.

The isolated human hepatocytes can be obtained from any one of a number of different sources. In one embodiment, the human hepatocytes were isolated from the liver of an organ donor. In another embodiment, the human hepatocytes were isolated from a surgical resection. In another embodiment, the human hepatocytes were derived from a stem cell, such as an embryonic stem cell, a mesenchymal-derived stem cell, an adipose tissue-derived stem cell, a multipotent adult progenitor cells or an unrestricted somatic stem cell. In another embodiment, the human hepatocytes were derived from monocytes or amniocytes, thus a stem cell or progenitor cell is obtained in vitro to produce hepatocytes. In another embodiment, the human hepatocytes were cryopreserved prior to injection.

Further provided herein is a method of serial transplantation of human hepatocytes in the Fah-deficient recipient mouse. The method comprises collecting the expanded human hepatocytes from a first recipient mouse and further expanding the hepatocytes in a second, third, fourth or additional recipient mouse. Human hepatocytes can be collected from a mouse using any one of a number of techniques. For example, the hepatocytes can be collected by perfusing the mouse liver, followed by gentle mincing, as described in the Examples below. Furthermore, the hepatocytes can be separated from other cell types, tissue and/or debris using well known methods, such as by using an antibody that specifically recognizes human cells, or human hepatocytes. Such antibodies include, but are not limited to an antibody that specifically binds to a class I major histocompatibility antigen, such as anti-human HLA-A,B,C (Markus et al. *Cell Transplantation* 6:455-462, 1997). Antibody bound hepatocytes can then be separated by panning (which utilizes a monoclonal antibody attached to a solid matrix), fluorescence activated cell sorting (FACS), magnetic bead separation or the like. Alternative methods of collecting hepatocytes are well known in the art.

Also provided herein is a genetically modified mouse whose genome is homozygous for deletions or point mutations in the Fah, Rag2 and Il2rg genes such that the deletions or point mutations result in loss of expression of functional FAH, RAG-2 and IL-2Rγ proteins, wherein the mouse is immunodeficient and exhibits decreased liver function, and wherein human hepatocytes can be expanded in the mouse. In one embodiment, the deletions result in the complete loss of B cells, T cells and NK cells. In another embodiment, the mouse expresses urokinase. In one embodiment, urokinase is human urokinase. In one aspect, expression of urokinase results from incorporation of a transgene encoding urokinase. In another aspect, expression of urokinase results from administration of a vector encoding urokinase, such as a secreted or non-secreted form of urokinase. The vector encoding urokinase can be any type of vector suitable for delivery to a mouse and capable of expressing the urokinase gene. In one embodiment, the vector is an adenovirus vector. In another embodiment, the vector is an AAV vector. In some embodiments the mouse is an FRG mouse. In some embodiments, the mouse is an $F^{pm}RG$ mouse.

IV. Genetically Modified Mouse Strain for Expansion of Human Hepatocytes

Several groups have attempted to engraft and expand primary human hepatocytes in rodents (U.S. Pat. No. 6,509,514; PCT Publication No. WO 01/07338; U.S. Publication No.

2005-0255591). Dandri et al. (*Hepatology* 33:981-988, 2001) were the first to report successful repopulation of mouse livers with human hepatocytes. Since then, other groups have reported successful engraftment of human liver cells in mice. In all of these studies, the animals used were transgenic animals expressing urokinase plasminogen activator (uPA) under the transcriptional control of an albumin promoter (Sandgren et al. *Cell* 66:245-256, 1991). Overexpression of uPA causes metabolic disruption, leading to cell death of the mouse hepatocytes without affecting the transplanted human hepatocytes, which do not express the transgene. The alb-uPA transgene was crossed onto various immune deficient backgrounds to prevent rejection of the human cells (Tateno et al. *Am. J. Pathol.* 165:901-912, 2004; Katoh et al. *J. Pharm. Sci.* 96:428-437, 2007; Turrini et al. *Transplant. Proc.* 38:1181-1184, 2006).

While engraftment levels of up to 70% have been reported in these models, the system has several major disadvantages which have prevented wide-spread use. First, the alb-uPA transgene becomes inactivated or lost early in life. For this reason, it is necessary to transplant human cells very early (14 days of age) and to use mice which are homozygous for the transgene. This narrow transplantation time window severely restricts the flexibility of the model. Second, the spontaneous inactivation of the transgene creates a pool of transgene-negative, healthy mouse hepatocytes. These revertant murine hepatocytes compete efficiently with human cells during repopulation. It is therefore not possible to repopulate secondary recipients upon serial transplantation of the human cells. Third, liver disease has a very early onset in this model, thus reducing the viability of the transgenic mice. Consequently, it is difficult to breed sufficient numbers of experimental animals. In addition, the transgenic mice have a bleeding tendency which increases mortality during surgery. Finally, alb-uPA transgenic animals develop renal disease once the repopulation with human cells exceeds 50%. This is thought to be due to the action of human complement on renal epithelium. To obtain very high levels of human engraftment it is necessary to treat the transplanted mice with an anti-complement protease inhibitor (Tateno et al. *Am. J. Pathol.* 165:901-912, 2004). Because of these many limitations, a more robust system for expanding human hepatocytes is highly desirable.

Described herein is a highly efficient method for expanding human hepatocytes in vivo using a genetically modified mouse having a unique combination of gene deletions. Successful engraftment and expansion of human hepatocytes in mouse liver requires an immunodeficient mouse with some degree of liver dysfunction. Mouse livers have been repopulated with human hepatocytes in a variety of different types of immunodeficient mice, including RAG-2 knockout or SCID mice, both of which lack B cells and T cells (U.S. Pat. No. 6,509,514; PCT Publication No. WO 01/07338; U.S. Publication No. 2005-0255591). To achieve liver dysfunction, immunodeficient mice were crossed with urokinase plasminogen activator (uPA) transgenic mice. Expression of uPA in the mouse liver creates a growth disadvantage for the mouse hepatocytes, which facilitates the expansion of transplanted human hepatocytes (PCT Publication No. WO 01/07338). To avoid the limitations of the uPA transgene, Fah-deficient mice were analyzed for their capacity to allow for expansion of human hepatocytes. FAH is a metabolic enzyme that catalyzes the last step of tyrosine catabolism. Mice having a homozygous deletion of the Fah gene exhibit altered liver mRNA expression and severe liver dysfunction (Grompe et al. *Genes Dev.* 7:2298-2307, 1993).

When the Fah mutation was crossed onto nude or Rag1$^{-/-}$ (Mombaerts et al. *Cell* 68:869-877, 1992) backgrounds, repopulation of mouse liver with human hepatocytes was not successful, most likely due to immune rejection. Crossing Fah-deficient mice with NOD/SCID mice (Dick et al. *Stem Cell* 15:199-203, 1997) produced mice in which occasional engraftment of human hepatocytes was observed; however, these animals developed rapid hepatic failure, potentially due to the double-strand break DNA repair defect present in SCID mice. It is disclosed herein that Fah$^{-/-}$/Rag2$^{-/-}$/Il2rg$^{-/-}$ (FRG) triple mutant mice lack T cells, B cells and NK cells. Rag2$^{-/-}$/Il2r$^{-/-}$ mice are known in the art (Traggiai et al. *Science* 304:104-107, 2004; Gorantla et al. *J. Virol.* 81:2700-2712, 2007).

As described in the Examples below, engraftment and expansion of human hepatocytes is surprisingly highly efficient in FRG mice. For example, an FRG mouse can be injected with one million isolated human hepatocytes. Assuming 10% efficiency, 100,000 human hepatocytes engraft in the recipient mouse. An average yield from an FRG mouse following expansion is then about 30 to about 45 million human hepatocytes, which equates to a 300- to 450-fold increase in human hepatocytes. FRG mice can also be used for serial transplantation of human hepatocytes. Serial transplantation can involve multiple mice and can result in at least about 150-fold expansion of human hepatocytes per mouse.

Any immunodeficient mouse comprising Fah-deficiency is suitable for the methods described herein. In one embodiment, the mouse is a Rag2$^{-/-}$/Il2rg$^{-/-}$ mouse which is also deficient in Fah. The Fah-deficient mouse can comprise, for example, homozygous deletions in Fah, or one or more point mutations in Fah. Fah-deficiency (such as by point mutation or homozygous deletion) results in a substantial decrease in, or the absence of, Fah mRNA expression and/or functional FAH protein. In addition to the FRG mouse, it is described herein that an immunodeficient mouse (Rag2$^{-/-}$/Il2rg$^{-/-}$) homozygous for a point mutation in the Fah gene (referred to herein as the F$^{pm}$RG mouse) also is a suitable mouse for engraftment and expansion of human hepatocytes in vivo.

V. Isolation and Delivery of Human Hepatocytes

A significant advantage of using Fah-deficient mice for the in vivo expansion of human hepatocytes is the ability to engraft the mice with human hepatocytes derived from a variety of sources. As described in the Examples below, human hepatocytes can be derived from cadaveric donors or liver resections, or can be obtained from commercial sources. In addition, as shown herein, FRG mice can be successfully transplanted with human hepatocytes from donors of all ages or with cryopreserved hepatocytes. There is often a delay (typically 1 to 2 days) between isolation of human hepatocytes and transplantation, which can result in poor viability of the hepatocytes. However, the FRG mouse system is capable of expanding human hepatocytes even when engrafted with hepatocytes of limited viability.

Methods of isolating human hepatocytes are well known in the art. For example, methods of isolating human hepatocytes from organ donors or liver resections are described in PCT Publication Nos. WO 2004/009766 and WO 2005/028640 and U.S. Pat. Nos. 6,995,299 and 6,509,514, all of which are herein incorporated by reference. Hepatocytes can be obtained from a liver biopsy taken percutaneously or via abdominal surgery. Human hepatocytes for transplantation into a recipient animal, such as an FRG mouse, are isolated from human liver tissue by any convenient method known in the art. Liver tissue can be dissociated mechanically or enzymatically to provide a suspension of single cells, or fragments of intact human hepatic tissue may be used. For example, the hepatocytes are isolated from donor tissue by routine collagenase perfusion (Ryan et al. *Meth. Cell Biol.* 13:29, 1976) followed by low-speed centrifugation. Hepatocytes can then be purified by filtering through a stainless steel mesh, followed by density-gradient centrifugation. Alternatively, other methods for enriching for hepatocytes can be used, such as, for example, fluorescence activated cell sorting, panning, magnetic bead separation, elutriation within a centrifugal field, or any other method well known in the art. Similar hepatocyte isolation methods can be used to collect expanded human hepatocytes from recipient mouse liver.

Alternatively, human hepatocytes can be prepared using the technique described by Guguen-Guillouzo et al. (*Cell Biol. Int. Rep.* 6:625-628, 1982), which is incorporated by reference. Briefly, a liver or portion thereof is isolated and a cannula is introduced into the portal vein or a portal branch. The liver tissue is then perfused, via the cannula, with a calcium-free buffer followed by an enzymatic solution containing collagenase (such as about 0.025% collagenase) in calcium chloride solution (such as about 0.075% calcium chloride) in HEPES buffer at a flow rate of between 30 and 70 milliliters per minute at 37° C. The perfused liver tissue is minced into small (such as about 1 cubic millimeter) pieces. The enzymatic digestion is continued in the same buffer as described above for about 10-20 minutes with gentle stirring at 37° C. to produce a cell suspension. The released hepatocytes are collected by filtering the cell suspension through a 60-80 micrometer nylon mesh. The collected hepatocytes can then be washed in cold HEPES buffer at pH 7.0 using slow centrifugation to remove collagenase and cell debris. Non-parenchymal cells may be removed by metrizamide gradient centrifugation (see U.S. Pat. No. 6,995,299).

Human hepatocytes can be obtained from fresh tissue (such as tissue obtained within hours of death) or freshly frozen tissue (such as fresh tissue frozen and maintained at or below about 0° C.). Preferably, the human tissue has no detectable pathogens, is normal in morphology and histology, and is essentially disease-free. The hepatocytes used for engraftment can be recently isolated, such as within a few hours, or can be transplanted after longer periods of time if the cells are maintained in appropriate storage media. One such media described in the Examples below is VIASPAN™ (a universal aortic flush and cold storage solution for the preservation of intra-abdominal organs; also referred to as University of Wisconsin solution, or UW).

Hepatocytes also can be cryopreserved prior to transplantation. Methods of cryopreserving hepatocytes are well known in the art and are described in U.S. Pat. No. 6,136,525, which is herein incorporated by reference.

In addition to obtaining human hepatocytes from organ donors or liver resections, the cells used for engraftment can be human stem cells or hepatocyte precursor cells which, following transplantation into the recipient animal, develop or differentiate into human hepatocytes capable of expansion. Human cells with ES cell properties have been isolated from the inner blastocyst cell mass (Thomson et al., *Science* 282: 1145-1147, 1998) and developing germ cells (Shamblott et al., *Proc. Natl. Acad. Sci. USA* 95:13726-13731, 1998), and human embryonic stem cells have been produced (see U.S. Pat. No. 6,200,806, which is incorporated by reference herein). As disclosed in U.S. Pat. No. 6,200,806, ES cells can be produced from human and non-human primates. Generally, primate ES cells are isolated on a confluent layer of murine embryonic fibroblast in the presence of ES cell medium. ES medium generally consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Distinguishing features of ES cells, as compared to the committed "multipotential" stem cells present in adults, include the capacity of ES cells to maintain an undifferentiated state indefinitely in culture, and the potential that ES cells have to develop into every different cell types. Human ES (hES) express SSEA-4, a glycolipid cell surface antigen recognized by a specific monoclonal antibody (see, for example, Amit et al., *Devel. Biol.* 227:271-278, 2000).

Human hepatocytes derived from human mesenchymal stem cells (hMSCs) can also be used in the methods described herein. Sequential exposure of bone marrow-derived hMSCs to hepatogenic factors results in differentiation of the stem cells to cells with hepatocyte properties (see Snykers et al. *BMC Dev Biol.* 7:24, 2007; Aurich et al. *Gut.* 56(3):405-15, 2007, each of which is incorporated herein by reference). Hepatogenic differentiation of bone marrow-derived mesenchymal stem cells and adipose tissue-derived stem cells (ADSCs) has also been described (see Talens-Visconti et al. *World J Gastroenterol.* 12(36):5834-45, 2006, incorporated herein by reference). Human hepatocytes can also be generated from monocytes. Ruhnke et al. (*Transplantation* 79(9):1097-103, 2005, incorporated herein by reference) describe the generation of hepatocyte-like (NeoHep) cells from terminally differentiated peripheral blood monocytes. The NeoHep cells resemble primary human hepatocytes with respect to morphology, expression of hepatocyte markers, various secretory and metabolic functions and drug detoxification activities. In addition, human hepatocytes derived from amniocytes, also can be used in the methods described herein.

Human ES cell lines exist and can be used in the methods disclosed herein. Human ES cells can also be derived from preimplantation embryos from in vitro fertilized (IVF) embryos. Experiments on unused human IVF-produced embryos are allowed in many countries, such as Singapore and the United Kingdom, if the embryos are less than 14 days old. Only high quality embryos are suitable for ES isolation. Present defined culture conditions for culturing the one cell human embryo to the expanded blastocyst have been described (see Bongso et al., *Hum Reprod.* 4:706-713, 1989). Co-culturing of human embryos with human oviductal cells results in the production of high blastocyst quality. IVF-derived expanded human blastocysts grown in cellular co-culture, or in improved defined medium, allows isolation of human ES cells (see U.S. Pat. No. 6,200,806).

In one embodiment, human hepatocytes are delivered to recipient mice by transplantation, such as by injection, into the spleen. Hepatocytes can be delivered by other means, such as by injection into liver parenchyma or the portal vein. The number of human hepatocytes injected into a recipient mouse can vary. In one embodiment, about $10^5$ to about $10^7$ human hepatocytes are injected. In another embodiment, about $5 \times 10^5$ to about $5 \times 10^6$ human hepatocytes are injected. In one exemplary embodiment, about $10^6$ human hepatocytes are injected.

VI. Use of Human Hepatocytes Expanded in Fah-deficient mice

Human hepatocytes can be collected from recipient mice using any of a number of techniques known in the art. For example, mice can be anesthetized and the portal vein or inferior vena cava cannulated with a catheter. The liver can then be perfused with an appropriate buffer (such as a calcium- and magnesium-free EBSS supplemented with 0.5 mM EGTA and 10 mM HEPES), followed by collagenase treatment (for example, using a solution was of EBSS supplemented with 0.1 mg/ml collagenase XI and 0.05 mg/ml DNase I). The liver can be gently minced and filtered through nylon mesh (such as sequentially through 70 μm and 40 μm nylon mesh), followed by centrifugation and washing of the cells.

Human hepatocytes collected from recipient mice can be separated from non-human cells or other contaminants (such as tissue or cellular debris) using any technique well known in the art. For example, such methods include using an antibody which selectively binds to human hepatocytes. Such antibodies include, but are not limited to an antibody that specifically binds to a class I major histocompatibility antigen, such as anti-human HLA-A,B,C (Markus et al. *Cell Transplantation* 6:455-462, 1997). Antibodies specific for human cells or human hepatocytes can be used in a variety of different techniques, including FACS, panning or magnetic bead separation. FACS employs a plurality of color channels, low angle and obtuse light-scattering detection channels, and impedance channels, among other more sophisticated levels of detection, to separate or sort cells (see U.S. Pat. No. 5, 061, 620) bound by the antibody. Magnetic separation involves the use of paramagnetic particles which are: 1) conjugated to the human specific antibodies; 2) conjugated to detection antibodies which are able to bind to the human specific antibodies; or 3) conjugated to avidin which can bind to biotinylated antibodies. Panning involves a monoclonal antibody attached to a solid matrix, such as agarose beads, polystyrene beads, hollow fiber membranes or plastic petri dishes. Cells that are bound by the antibody can be isolated from a sample by simply physically separating the solid support from the sample.

As described in the Examples below, expression of genes involved in drug conjugation and detoxification, including several of the hepatocyte transporter proteins, was detected in expanded human hepatocytes collected from recipient mice. Recent studies have shown the critical role played by these conjugation pathways (Kostrubsky et al. *Drug. Metab. Dispos.* 28:1192-1197, 2000) and hepatocyte transporter proteins (Kostrubsky et al. *Toxicol. Sci.* 90:451-459, 2006) in predicting drug toxicity. Along with a normal human response to CYP induction by exogenous drugs, such as rifampicin or PB, or BNF, the expression of the nuclear hormone receptor transcription factors, the conjugation pathways and major transport proteins by the human hepatocytes expanded in FRG mice allow for the assessment of the role of these gene products in human drug metabolism and toxicity, in vivo. Methods of testing toxicity of compounds in isolated hepatocytes are well known in the art and are described, for example, in PCT Publication No. WO 2007/022419, which is herein incorporated by reference.

The present disclosure further contemplates the use of human hepatocytes expanded in and collected from recipient mice as a source of human hepatocytes for liver reconstitution in a subject in need of such therapy. Reconstitution of liver tissue in a patient by the introduction of hepatocytes is a potential therapeutic option for patients with acute liver failure, either as a temporary treatment in anticipation of liver transplant or as a definitive treatment for patients with isolated metabolic deficiencies (Bumgardner et al. *Transplantation* 65: 53-61, 1998). Hepatocyte reconstitution may be used, for example, to introduce genetically modified hepatocytes for gene therapy or to replace hepatocytes lost as a result of disease, physical or chemical injury, or malignancy (U.S. Pat. No. 6,995,299, herein incorporated by reference). For example, use of transfected hepatocytes in gene therapy of a patient suffering from familial hypercholesterolemia has been reported (Grossman et al. *Nat. Genet.* 6: 335, 1994). In addition, expanded human hepatocytes can be used to populate artificial liver assist devices.

Human hepatocytes expanded in and collected from FRG mice are also useful for a variety of microbiological studies. A number of pathogenic viruses, including hepatitis C virus and hepatitis B virus, will only replicate in a human host or in primary human hepatocytes. Thus, having a sufficient source of primary human hepatocytes is critical for studies of these pathogens. The expanded human hepatocytes can be used for studies of viral infection and replication or for studies to identify compounds that modulate infection of hepatic viruses. Methods of using primary human hepatocytes for studies of hepatic viruses are described in European Patent No. 1552740, U.S. Pat. No. 6,509,514 and PCT Publication No. WO 00/17338, each of which is herein incorporated by reference.

VII. Use of Fah-Deficient Mice as a Model System for Human Liver Disease

Immunodeficient, Fah-deficient mice can also be used as a model system for human liver disease. These mice, including $Rag2^{-/-}/Il2rg^{-/-}$ mice further comprising Fah deficiency (such as, for example FRG or $F^{pm}RG$ mice) engrafted with human hepatocytes can be used to create models of liver disease resulting from a variety of different causes, including, but not limited to, exposure to a toxin, infectious disease, genetic disease or malignancy. Fah-deficient mice engrafted and reconstituted with human hepatocytes can be used to gain a better understanding of these diseases and to identify agents which may prevent, retard or reverse the disease processes. For example, Fah-deficient mice can be used to test gene therapy vectors. A gene therapy vector of interest can be administered to the Fah-deficient mouse and the effects of the vector on the engrafted human hepatocytes can be evaluated.

Similarly, Fah-deficient mice comprising human hepatocytes can be used to screen compounds, such as toxins or pharmaceutical agents, for their effect on human hepatocytes in an in vivo setting. An agent suspected of causing or contributing to a hepatic disease can be screened by administering an effective amount of an agent to an Fah-deficient mouse and assessing the effect of the agent upon function of the engrafted human cells. As one example, an Fah-deficient mouse can be used to identify an agent that inhibits or prevents infection by a hepatotrophic pathogen. To identify such as agent, an Fah-deficient mouse can be exposed to or inoculated with a pathogen, followed by, or preceded by, being administered a test agent. The mouse can then be evaluated for signs of infection and optionally compared to control mice that have not been treated with the agent and/or have not been infected by the pathogen.

Where an Fah-deficient mouse is to be used as a model for liver disease caused by a toxin, the injected human hepatocytes must engraft and be allowed to expand for a suitable period of time prior to exposure to the toxic agent. The amount of time required for hepatocyte expansion can be determined empirically and is within the capabilities of one of ordinary skill in the art. The amount of toxic agent required to produce results most closely mimicking the corresponding human condition may be determined by using a number of Fah-deficient mice exposed to incremental doses of the toxic agent. Examples of toxic agents include but are not limited to alcohol, acetaminophen, phenytoin, methyldopa, isoniazid, carbon tetrachloride, yellow phosphorous, and phalloidin.

In embodiments where a Fah-deficient mouse is to be used as a model for malignant liver disease, the malignancy may be produced by exposure to a transforming agent or by the introduction of malignant cells. The transforming agent or malignant cells may be introduced with the initial colonizing introduction of human hepatocytes or, preferably, after the human hepatocytes have begun to proliferate in the host animal. In the case of a transforming agent, it may be preferable to administer the agent at a time when human hepatocytes are actively proliferating. Such transforming agents may be administered either systemically to the animal or locally into the liver itself. Malignant cells can be inoculated directly into the liver. As one example, a Fah-deficient mouse is transplanted with human hepatocytes. Following engraftment of the human hepatocytes, the mouse is administered a transforming agent or is inoculated with malignant cells. Alternatively, the transforming agent or malignant cells can be administered in conjunction with the human hepatocytes. After a malignancy has developed in the mouse, which can be determined by any one of a number of methods known in the art, the Fah-deficient mouse can be used as a model for human hepatic cancer.

VIII. Vectors Encoding Urokinase

In some embodiments of the methods described herein, Fah-deficient mice are administered a vector encoding urokinase prior to transplantation of human hepatocytes. In one embodiment, the urokinase (also known as urokinase plasminogen activator (uPA)) is the secreted form of human urokinase. In another embodiment, the urokinase is a modified, non-secreted form of urokinase (see U.S. Pat. No. 5,980,886, incorporated herein by reference). Any type of suitable vector for expression of urokinase in mice is contemplated. Such vectors include plasmid vectors or viral vectors. Suitable vectors include, but are not limited to, DNA vectors, adenovirus vectors, retroviral vectors, pseudotyped retroviral vectors, AAV vectors, gibbon ape leukemia vector, VSV-G, VL30 vectors, liposome mediated vectors, and the like. In one embodiment, the viral vector is an adenovirus vector. The adenovirus vector can be derived from any suitable adenovirus, including any adenovirus serotype (such as, but not limited to Ad2 and Ad5). Adenovirus vectors can be first, second, third and/or fourth generation adenoviral vectors or gutless adenoviral vectors. The non-viral vectors can be constituted by plasmids, phospholipids, liposomes (cationic and anionic) of different structures. In another embodiment, the viral vector is an AAV vector. The AAV vector can be any suitable AAV vector known in the art.

Viral and non-viral vectors encoding urokinase are well known in the art. For example, an adenovirus vector encoding human urokinase is described in U.S. Pat. No. 5,980,886 and by Lieber et al. (*Proc. Natl. Acad. Sci. U.S.A.* 92(13):6210-4, 1995). U.S. Pat. Application Publication No. 2005-176129 and U.S. Pat. No. 5,585,362 describe recombinant adenovirus vectors and U.S. Pat. No. 6,025,195 discloses an adenovirus vector for liver-specific expression. U.S. Pat. Application Publication No. 2003-0166284 describes adeno-associated virus (AAV) vectors for liver-specific expression of a gene of interest, including urokinase. U.S. Pat. Nos. 6,521,225 and 5,589,377 describe recombinant AAV vectors. PCT Publication No. WO 0244393 describes viral and non-viral vectors comprising the human urokinase plasminogen activator gene. An expression vector capable of high level of expression of the human urokinase gene is disclosed in PCT Publication No. WO 03087393. Each of the aforementioned patents and publications are herein incorporated by reference.

Vectors encoding urokinase can optionally include expression control sequences, including appropriate promoters, enhancers, transcription terminators, a start codon (i.e., ATG) in front of a protein-encoding gene, splicing signal for introns and maintenance of the correct reading frame of that gene to permit proper translation of mRNA, and stop codons. Generally expression control sequences include a promoter, a minimal sequence sufficient to direct transcription.

The expression vector can contain an origin of replication, a promoter, as well as specific genes which allow phenotypic selection of the transformed cells (such as an antibiotic resistance cassette). Generally, the expression vector will include a promoter. The promoter can be inducible or constitutive. The promoter can be tissue specific. Suitable promoters include the thymidine kinase promoter (TK), metallothionein I, polyhedron, neuron specific enolase, thyrosine hyroxylase, beta-actin, or other promoters. In one embodiment, the promoter is a heterologous promoter.

In one example, the sequence encoding urokinase is located downstream of the desired promoter. Optionally, an enhancer element is also included, and can generally be located anywhere on the vector and still have an enhancing effect. However, the amount of increased activity will generally diminish with distance.

The vector encoding urokinase can be administered by a variety of routes, including, but not limited to, intravenously, intraperitoneally or by intravascular infusion via portal vein. The amount of vector administered varies and can be determined using routine experimentation. In one embodiment, FRG mice are administered an adenovirus vector encoding urokinase at a dose of about $1\times10^8$ to about $1\times10^{10}$ plaque forming units. In one preferred embodiment, the dose is about $5\times10^9$ plaque forming units.

In one exemplary embodiment, FRG mice are administered an adenovirus vector encoding human urokinase. Adenovirus vectors have several advantages over other types of viral vectors, such as they can be generated to very high titers of infectious particles; they infect a great variety of cells; they efficiently transfer genes to cells that are not dividing; and they are seldom integrated in the guest genome, which avoids the risk of cellular transformation by insertional mutagenesis (Douglas and Curiel, *Science and Medicine*, March/April 1997, pages 44-53; Zern and Kresinam, *Hepatology*:25(2), 484-491, 1997). Representative adenoviral vectors which can be used to encode urokinase are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (Gene Therapy, 2:151-155, 1995), which are herein incorporated by reference.

The following examples are provided to illustrate certain particular features and/or embodiments. These examples should not be construed to limit the invention to the particular features or embodiments described.

EXAMPLES

As described in the following Examples, engraftment and expansion of human hepatocytes is highly efficient in FRG mice. FRG livers are macroscopically normal in size and shape and histological examination reveals no significant differences from immune-competent Fah$^{-/-}$ mice. In addition, FRG mice grow well and are fully fertile when administered NTBC.

In one embodiment, in FRG mice the extent of liver disease and selective pressure can be controlled by administering and withdrawing NTBC (Grompe et al. *Nat. Genet.* 10:453-460, 1995). Withdrawal of NTBC provides a selective advantage for the transplanted human hepatocytes. Being able to readily control the extent of liver disease makes animal husbandry and surgery much easier. Furthermore, the Fah-deficiency mutation is a deletion and cannot revert back to wild-type by transgene inactivation. Therefore, competition from endogenous revertant mouse cells does not exist in Fah knockout livers. This means that FRG mice can be engrafted with human hepatocytes at any age and that serial transplantation is feasible. Also of significance, FRG mice can be highly repopulated without administration of a complement inhibitor, which previous studies have shown is required to prevent renal disease when repopulation with human cells exceeds 50% (Tateno et al. *Am. J. Pathol.* 165:901-912, 2004). This is not only of practical importance in animal husbandry, but also removes a potential source of pharmacological interference.

The repopulation efficiency of human hepatocytes in FRG mice can exceed about 70% (70% or more of the hepatocytes in the mouse liver are human). An average yield from a single repopulated FRG mouse is approximately 30-45 million human hepatocytes. Expanded hepatocytes from a single FRG mouse can then be used to repopulate up to 100 secondary FRG recipient mice, in a process termed serial transplantation.

Serial transplantation can be achieved in the new system described herein. Not only does serial transplantation allow for extensive human hepatocyte expansion, it provides a means for expanding human cells of the same genotype through several generations of recipient mice. It also signifies that a high quality source of human hepatocytes for further transplantation is always in hand. It is demonstrated herein that at least four rounds of hepatocyte transplantation is feasible. In addition, the viability of human hepatocytes isolated from serial transplantation can exceed about 80% and the hepatocytes readily attach to collagen-coated plates. Based on an estimate of 10% engraftment efficiency (100,000 cells) and a final harvest of about 15 million expanded human hepatocytes after repopulation, an in vivo expansion of at least 150-fold can be achieved in each round. Thus, total expansion of human hepatocytes in FRG mice can exceed 500 million-fold.

Engraftment and expansion of human hepatocytes is possible in FRG mice using isolated human hepatocytes from a variety of sources and of variable quality. Sources of human hepatocytes include, but are not limited to, cadaveric donors, liver resections and commercially available sources. As shown herein, engraftment and expansion of human hepatocytes was successful using donors of any age. Furthermore, human hepatocytes are demonstrated herein to be successfully expanded in FRG mice even when the hepatocytes were previously cryopreserved. This is a significant advantage over systems which require immediate transplantation after hepatocyte isolation.

Example 1

Generation of $Fah^{-/-}/Rag2^{-/-}/Il2rg^{-/-}$ (FRG) Mice

Several strains of immune-deficient Fah knockout mice were generated. Crossing the Fah mutation onto nude, nod/scid or $Rag1^{-/-}$ backgrounds was unsuccessful. To generate an immunodeficient $Fah^{-/-}$ mouse strain completely lacking T cells, B cells and NK cells, but without a DNA repair defect, $Fah^{-/-}/Rag2^{-/-}/Il2rg^{-/-}$ (FRG) mice were generated. Male $Fah^{-/-}$129S4 mice (Grompe et al. *Genes Dev.* 7:2298-2307, 1993) were crossed with female $Rag2^{-/-}/Il2rg^{-/-}$ mice (Taconic). All animals were maintained with drinking water containing 2-(2-nitro-4-trifluoro-methyl-benzoyl)-1,3 cyclohexanedione (NTBC) at a concentration of 1.6 mg/L (Grompe et al. *Nat. Genet.* 10:453-460, 1995). To confirm the genotypes of each animal, PCR-based genotyping was carried out on 200 ng genomic DNA isolated from toe tissue (Grompe et al. *Genes Dev.* 7:2298-2307, 1993; Traggiai et al. *Science* 304:104-107, 2004).

FRG mice grew well and were fully fertile if they were continuously given NTBC in their drinking water. FRG mouse livers were macroscopically normal in size and shape, and histological examination showed no differences between conventional $Fah^{-/-}$ mice and the FRG mice. As in conventional $Fah^{-/-}$ mice, NTBC withdrawal resulted in gradual hepatocellular injury in FRG mice and eventual death after 4-8 weeks (Overturf et al. *Nat. Genet.* 12:266-273, 1996).

Example 2

Histology and Engraftment Detection Assays

Histology and immunocytochemistry

FAH immunohistochemistry was performed as previously described (Wang et al. *Am. J. Pathol.* 161:565-574, 2002). Briefly, liver and kidney tissues fixed in 10% phosphate-buffered formalin, pH 7.4, were dehydrated in 100% ethanol and embedded in paraffin wax at 58° C. Deparaffinized 4-μm sections were stained with hematoxylin and eosin. For immunohistochemistry, sections were treated with 3% $H_2O_2$ in methanol for endogenous peroxydase blocking. Avidin and biotin blocking was also performed before incubation with primary antibodies. Sections were incubated with anti-FAH rabbit antibody or HepPar antibody (DAKO) for 2 hours at room temperature followed by HRP-conjugated secondary antibody incubation. Signals were detected by diaminobenzidine (DAB).

FAH Enzyme Assay

Fumarylacetoacetate was incubated with cytosolic liver fractions from recipient liver, and disappearance speed was measured spectroscopically at 330 nm. Wild type and $Fah^{-/-}$ livers were used as positive and negative control respectively. Fumarylacetoacetate was prepared enzymatically from homogentisic acid (Knox et al. *Methods Enzymol.* 2:287-300, 1955).

Genomic PCR for Alu sequence

Genomic DNA was isolated from the liver using the DNeasy tissue kit (Qiagen). Human Alu sequences were amplified by PCR according to standard procedures with the following primers 5'-GGCGCGGTGGCTCACG-3' (SEQ ID NO: 1) and 5'-TTTTTTGAGACGGAGTCTCGCTC-3' (SEQ ID NO: 2).

RT-PCR for hepatocyte specific gene expression

Total RNA was isolated from the liver using the RNeasy mini kit (Qiagen). Complementary DNA was synthesized by reverse transcriptase with an oligo-dT primer. The primers shown in Table 1 were used for human or mouse specific cDNA amplification.

TABLE 1

RT-PCR Primers for Amplification of Hepatocyte Specific Genes

| Primer Sequence | Primer Description | SEQ ID NO: |
|---|---|---|
| ATGGATGATTTCGCAGCTTT | human ALB forward | 3 |
| TGGCTTTACACCAACGAAAA | human ALB reverse | 4 |
| TACAGCGGAGCAACTGAAGA | mouse Alb forward | 5 |
| TTGCAGCACAGAGACAAGAA | mouse Alb reverse | 6 |

TABLE 1-continued

RT-PCR Primers for Amplification
of Hepatocyte Specific Genes

| Primer Sequence | Primer Description | SEQ ID NO: |
|---|---|---|
| CCGGGAGAGTTTTACCACAA | human TAT forward | 7 |
| CCTTCCCTAGATGGGACACA | human TAT reverse | 8 |
| CTGACCTCACCTGGGACAAT | human TF forward | 9 |
| CCTCCACAGGTTTCCTGGTA | human TF reverse | 10 |
| TTTGGGACCACTGTCTCTCC | human FAH forward | 11 |
| CTGACCATTCCCCAGGTCTA | human FAH reverse | 12 |
| ATGGCTTCTCATCGTCTGCT | human TTR forward | 13 |
| GCTCCTCATTCCTTGGGATT | human TTR reverse | 14 |
| GTGCCTTTATCACCCATGCT | human UGT1A1 forward | 15 |
| TCTTGGATTTGTGGGCTTTC | human UGT1A1 reverse | 16 |

Human Albumin Measurement

Small amounts of blood were collected once a week from the left saphenous vein with a heparinized blood capillary. After 1,000 or 10,000× dilution with Tris-buffered saline, human albumin concentration was measured with the Human Albumin ELISA Quantitation Kit (Bethyl) according to the manufacturer's protocol.

Fluorescent Immunocytochemistry

Hepatocytes from humanized mouse livers were suspended in Dulbecco's modified Eagle's medium (DMEM) and plated on collagen type1-coated 6-well plates. Attached cells were fixed with 4% paraformaldehyde for 15 minutes and blocked with 5% skim milk. Rabbit anti-FAH, goat anti-human albumin (Bethyl), goat anti-mouse albumin (Bethyl) were used as primary antibodies at dilution of 1/200. ALEXA™ Fluoro 488 anti-goat IgG (Invitrogen) or ALEXA™ Fluoro 555 anti-rabbit IgG (Invitrogen) were used as secondary antibody. The images were captured with an AXIOVERT™ 200 microscope by using Nikon digital camera.

FACS Analysis

After dissociation of the recipient livers, parenchymal cells were incubated at 4° C. for 30 minutes with fluorescein isothiocyanate (FITC)-conjugated anti-human human leukocyte antigen (HLA)-A,B,C (BD Pharmingen) and phycoerythrin (PE)-conjugated anti-mouse H2-K(b) (BD Pharmingen) antibodies. They were then rinsed with PBS twice and analyzed with a FACS CALIBUR™ (Becton Dickinson) flow cytometer. FITC-conjugated and PE-conjugated IgG were used as negative controls.

Fluorescence In Situ Hybridization

Total genomic DNA probes were generated by nick translation of total mouse and human genomic DNA. Cy3-dUTP incorporation was carried out according to manufacturer's recommendations (Invitrogen). Final probe concentration was 200 ng/μl. Slides with attached cells were treated with RNase at 100 mg/ml for 1 hour at 37° C. and washed in 2X SSC for three 3-minute rinses. Following wash steps, slides were dehydrated in 70, 90 and 100% ethanol for 3 min each. Chromosomes were denatured at 75° C. for 3 minutes in 70% formamide/2× SSC, followed by dehydration in ice cold 70%, 90% and 100% ethanol for 3 minutes each. Probe cocktails were denatured at 75° C. for 10 minutes and pre-hybridized at 37° C. for 30 minutes. Probes were applied to slides and incubated overnight at 37° C. in a humid chamber. Post-hybridization washes consisted of three 3-minute rinses in 50% formamide/2× SSC and three 3-minute rinses in PN buffer (0.1 M Na2HPO4, 0.1 M NaH2PO4, pH 8.0, 2.5% NONIDET™ P-40), all at 45° C. Slides were then counterstained with Hoechst (0.2 ug/ml), cover-slipped and viewed under UV fluorescence (Zeiss).

Example 3

Isolation and Cryopreservation of Human Hepatocytes

Human hepatocytes were isolated from donor livers that were not used for liver transplantation according to previously described procedures (Strom et al. *Cell Transplant.* 15:S105-110, 2006). Briefly, liver tissue was perfused with calcium and magnesium-free Hanks' balanced salt solution (Cambrex) supplemented with 0.5 mM EGTA (Sigma) and HEPES (Cellgro), followed by digestion with 100 mg/L collagenase XI (Sigma) and 50 mg/L deoxyribonuclease I (Sigma) in Eagle's minimal essential medium (Cambrex) through the existing vasculature. The cells were washed three times with Eagle's minimal essential medium plus 7% bovine calf serum (Hyclone) at 50×g for 2 minutes. Pelleted hepatocytes were transferred into cold VIASPAN™ (a universal aortic flush and cold storage solution for the preservation of intra-abdominal organs; also referred to as University of Wisconsin solution, or UW).

Shipped hepatocytes were transferred into VIASPAN™ solution supplemented with 10% fetal bovine serum and 10% dimethylsulfoxide at $5 \times 10^6$ hepatocytes per ml. The cryotubes were thickly wrapped with paper towels, stored at −80° C. for one day and finally transferred into liquid nitrogen. For thawing, cells were rapidly reheated in a 37° C. water bath and DMEM was added gradually to minimize the speed of change of the DMSO concentration.

Example 4

Repopulation of FRG mouse Liver with Human Hepatocytes

Overexpression of urokinase has been shown to enhance hepatocyte engraftment in several systems (Lieber et al. *Hum. Gene Ther.* 6:1029-1037, 1995). Therefore, experiments were performed to determine whether administration of a urokinase expressing adenovirus prior to transplantation of human hepatocytes would be beneficial. The adenoviral vector expressing the secreted form of human urokinase (urokinase plasminogen activator; uPA) has been previously described (Lieber et al. *Proc. Natl. Acad. Sci. U.S.A.* 92:6210-6214, 1995 and U.S. Pat. No. 5,980,886, herein incorporated by reference).

Donor hepatocytes were isolated and transplanted 24-36 hours after isolation. In the majority of cases, the cells were preserved in VIASPAN™ solution and kept at 4° C. during transport. However, in two experiments, cryopreserved hepatocytes were transplanted. The viability and quality of donor hepatocytes was highly variable with plating efficiencies ranging from 10% to 60%.

For transplantation, the following general protocol was used. Adult (6 to 15 week old) male or female FRG mice were given an intravenous injection (retroorbital) of uPA adenovirus ($5 \times 10^9$ plaque forming units (PFU) per mouse) 24-48 hours before transplantation. One million viable human hepatocytes (determined by trypan blue exclusion) in 100 µl of Dulbecco's modified essential medium were injected intrasplenically via a 27 gauge needle. NTBC was gradually withdrawn over the next six days (1.6 mg/L day 0-2; 0.8 mg/L day 3-4; 0.4 mg/L day 5-6) and completely withdrawn one week after transplantation. Two weeks after stopping NTBC, the animals were put back on the drug for five days and then taken off again.

In three separate transplantations, primary engraftment of human hepatocytes was observed in FRG mice in recipients which had first received the uPA adenovirus. The uPA-pretreatment regimen was therefore used in most subsequent transplantation experiments.

In total, human hepatocytes from nine different donors were used successfully and no engraftment failures occurred after introduction of the uPA adenovirus regimen. Of these, seven were isolated from the livers of brain-dead organ donors and two were isolated from surgical liver resections. Donor ages varied from 1.2 to 64 years (Table 2).

TABLE 2

Summary of Engraftment Results from each Hepatocyte Donor

| Donor | Origin | Age (years) | Number of mice transplanted | Human albumin positive (%) |
|---|---|---|---|---|
| A | cadaveric | 1.8 | 6 | N/A |
| B | resection | 55 | 9 | 3 (33) |
| C | resection | 50 | 5 | 1 (20) |
| D | cadaveric | 1.2 | 2 | 1 (50) |
| E | cadaveric (cryopreserved) | 55 | 5 | 2 (40) |
| G | commercial (cryopreserved) | N/A | 8 | 1 (13) |
| H | cadaveric | 64 | 6 | 2 (33) |
| I | cadaveric | 59 | 5 | 3 (60) |
| J | cadaveric | 1.3 | 6 | 4 (60) |

In all experiments, at least one recipient became significantly engrafted (>1% human cells) with human hepatocytes using this protocol, regardless of the cell batch used. Engraftment was demonstrated by different methods including histology, DNA analysis, enzyme assay and in later experiments, human serum albumin. In the transplantations monitored by albumin levels, 17 of 43 (39.5%; range 12 to 67%) primary recipients became repopulated (Table 2 and FIG. 3). Of these, seven were highly repopulated (30-90%) and achieved albumin levels >1 mg/ml. Not only hepatocytes from cadaveric livers, but also from hepatic resections, were engrafted. Furthermore, cryopreserved cells were also successfully engrafted.

Figure 1B:
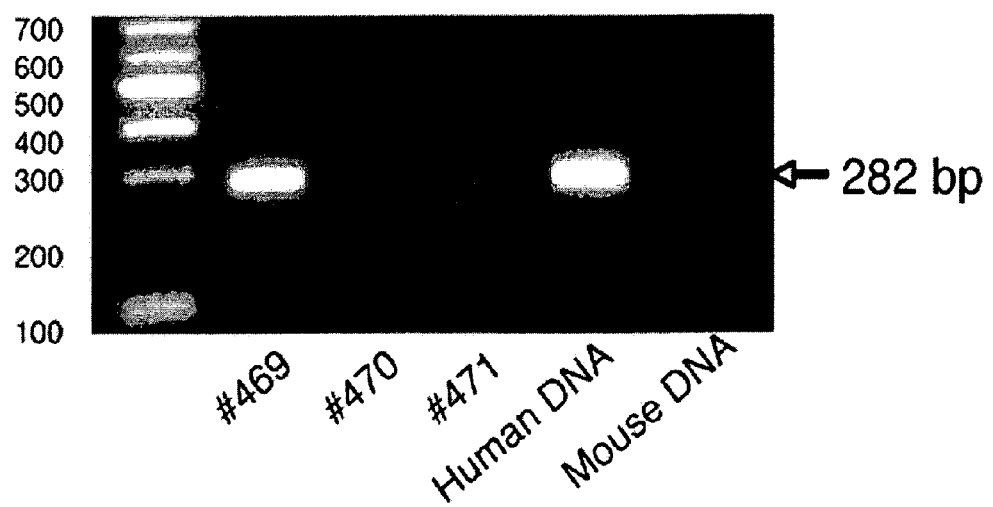
FIG. 1b is a digital image of a gel showing PCR amplification products of human Alu sequence on genomic DNA from hepatocyte-recipient livers. Only FRG mice were positive.

In highly engrafted mice (>30% repopulation), the weight of transplanted FRG mice stabilized during the second NTBC withdrawal, whereas fewer immune deficient litter mates heterozygous for Il2rg (Fah$^{-/-}$/Rag2$^{-/-}$/Il2rg$^{+/-}$) given the same cells continued to lose weight (FIG. 1a). This weight stabilization in triple mutant mice suggested that the transplanted human hepatocytes were replacing the functions of the diseased Fah$^{-/-}$ recipient hepatocytes. Upon complete weight stabilization (2-3 months after initial transplantation), the recipient livers were then harvested. Macroscopically, FRG livers were normal in shape and weight and without macroscopic nodules. Genomic PCR for human-specific Alu DNA-sequences was positive in FRG recipient livers, whereas Il2rg heterozygotes were all negative (FIG. 1b). To directly confirm hepatocytic function of the repopulating cells, FAH enzyme activity was assayed (Knox et al. *Methods Enzymol.* 2:287-300, 1955).

Figure 1C:
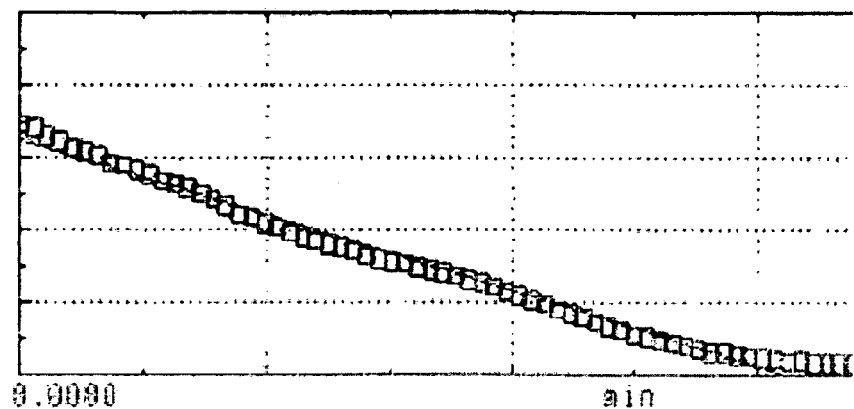
FIGS. 1c-e are graphs showing FAH enzyme activity in wild-type (FIG. 1c), Fah(−/−) (FIG. 1d) and humanized mouse liver (FIG. 1e). FAH substrate concentration declined in wild type mouse liver, but did not change with Fah$^{−/−}$ mouse liver. Humanized mouse liver showed ample enzyme activity.
Figure 1D:
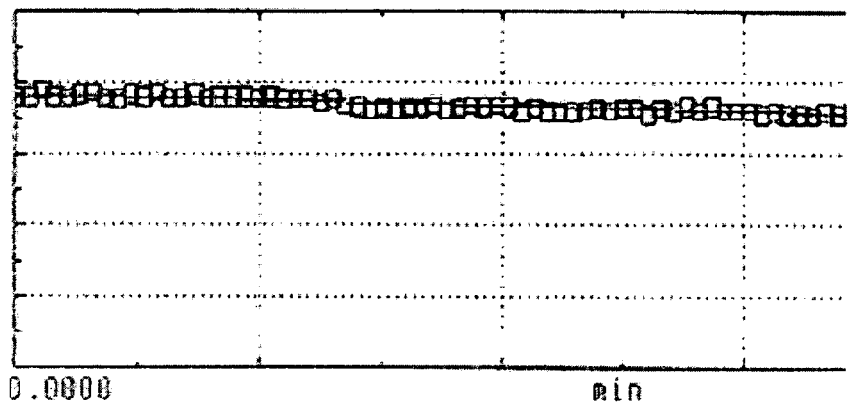
Figure 1E:
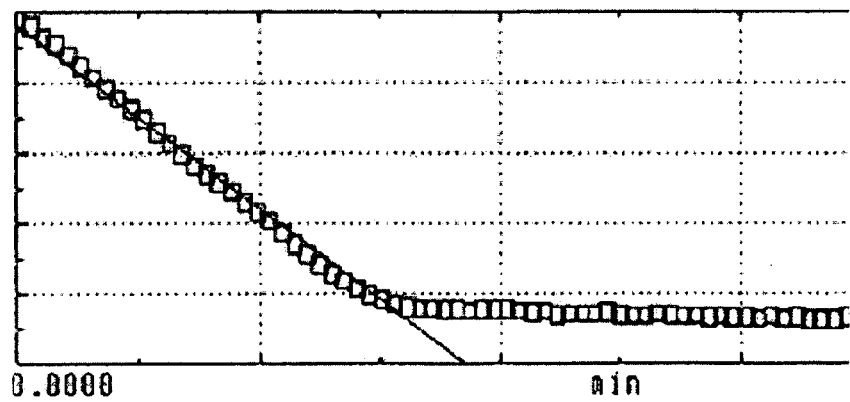
Figure 1F:
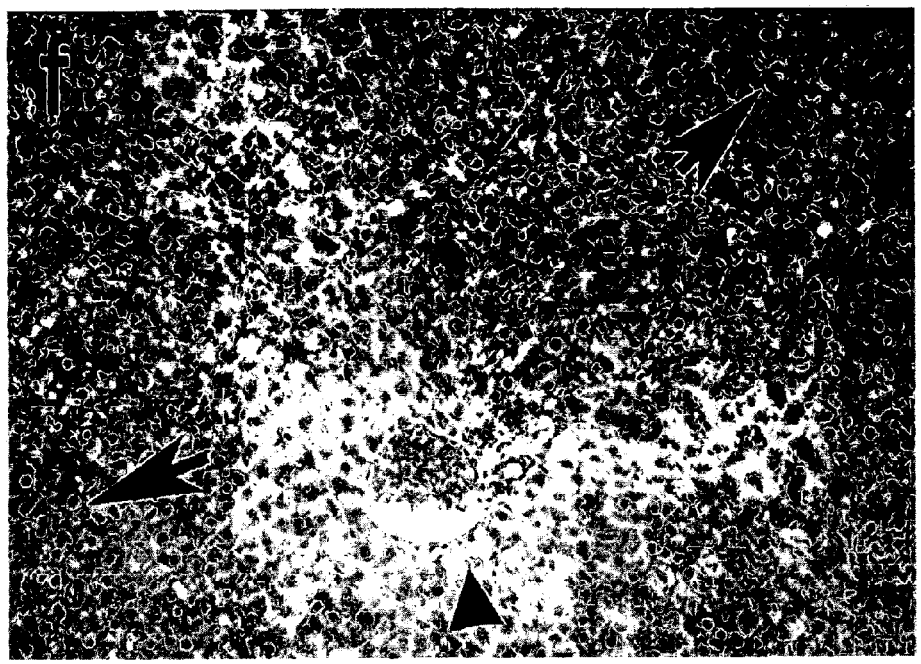
FIG. 1f is a digital image of FAH immunostaining in a repopulated mouse liver showing more than 80% of hepatocytes are positive for FAH (indicated by dark staining and the large arrows). The small arrow demarks FAH negative cells.
Figure 1G:
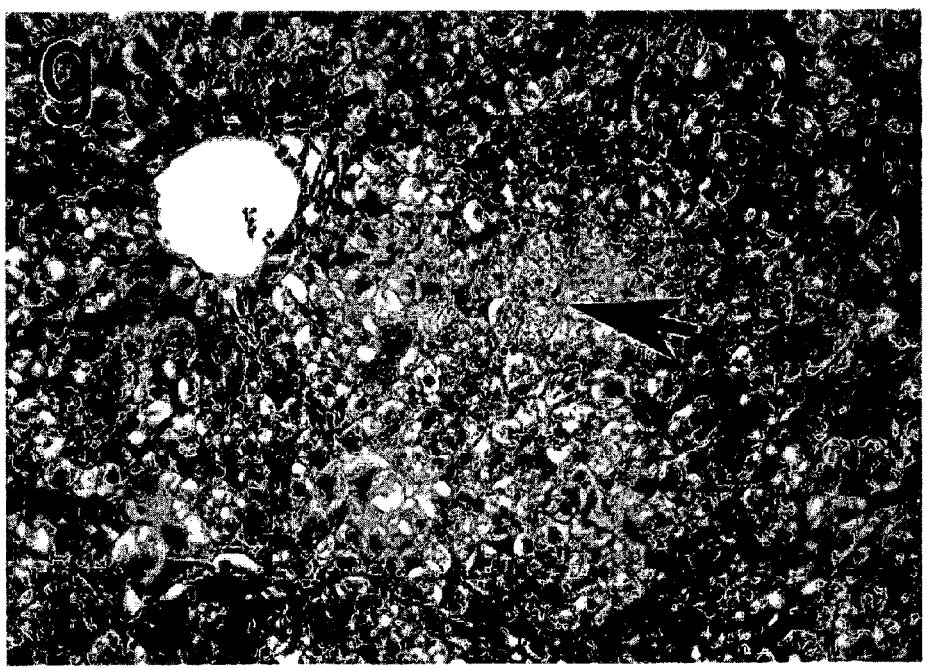
FIG. 1g is a digital image of H&E staining of the same liver section, which shows that human hepatocytes are less eosinophilic (indicated by the arrow). Original magnification ×200.

Recipient mouse livers had considerable amounts of FAH enzyme activity, equaling or exceeding normal mouse liver (FIGS. 1c-e). As FAH is expressed exclusively in fully differentiated hepatocytes, this suggested the transplanted human hepatocytes were not dedifferentiated or abnormal when engrafted in mouse liver. FAH immunostaining confirmed that more than 70% of liver parenchyma was repopulated with FAH-positive human hepatocytes (FIG. 1f and FIG. 1g).

Histological and immunohistochemical examination was performed using additional recipient livers (FIG. 2a and FIG. 2b). FAH-positive human hepatocytes appeared completely integrated into the structure of the recipient liver. In several recipients, the engrafted hepatocytes occupied more than of 80% parenchyma without disturbing the recipient liver organization (FIGS. 2b, 2e and 2f). Clonally expanding human hepatocytes could be clearly distinguished from mouse hepatocytes morphologically, by size, and by their pale cytoplasm (FIG. 2c and FIG. 2d). The size of human hepatocytes was relatively large, and their cytoplasm looked bright, probably because of glycogen accumulation as previously reported (Meuleman et al. *Hepatology* 41:847-856, 2005). FAH-positive hepatocytes were also positive for HepPar antibody, which specifically labels human hepatocytes but not mouse counterparts (FIG. 2e and FIG. 2f). In contrast, the FAH-negative areas displayed necroinflammation and contained dysplastic hepatocytes consistent with the findings in conventional Fah$^{-/-}$ mice after NTBC withdrawal.

Figure 3A:
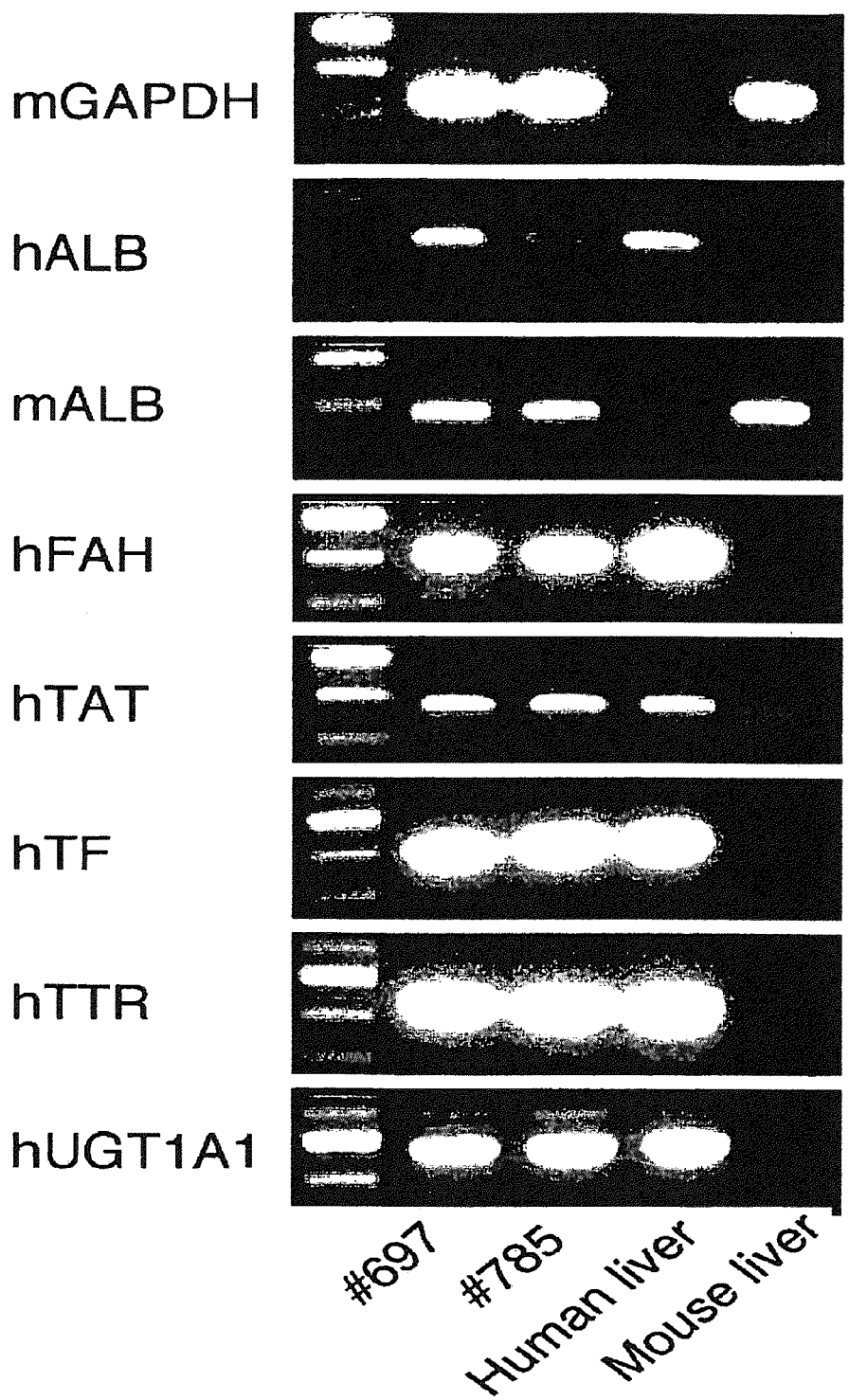
FIG. 3a is a series of gel sections showing RT-PCR products from chimeric mouse liver. The human ALB, FAH, TAT, TF, TTR, and UGT1A1 genes were expressed in chimeric mice livers (#697 and #785). Human hepatocytes and mouse hepatocytes were used as positive and negative control respectively.
Figure 3D:
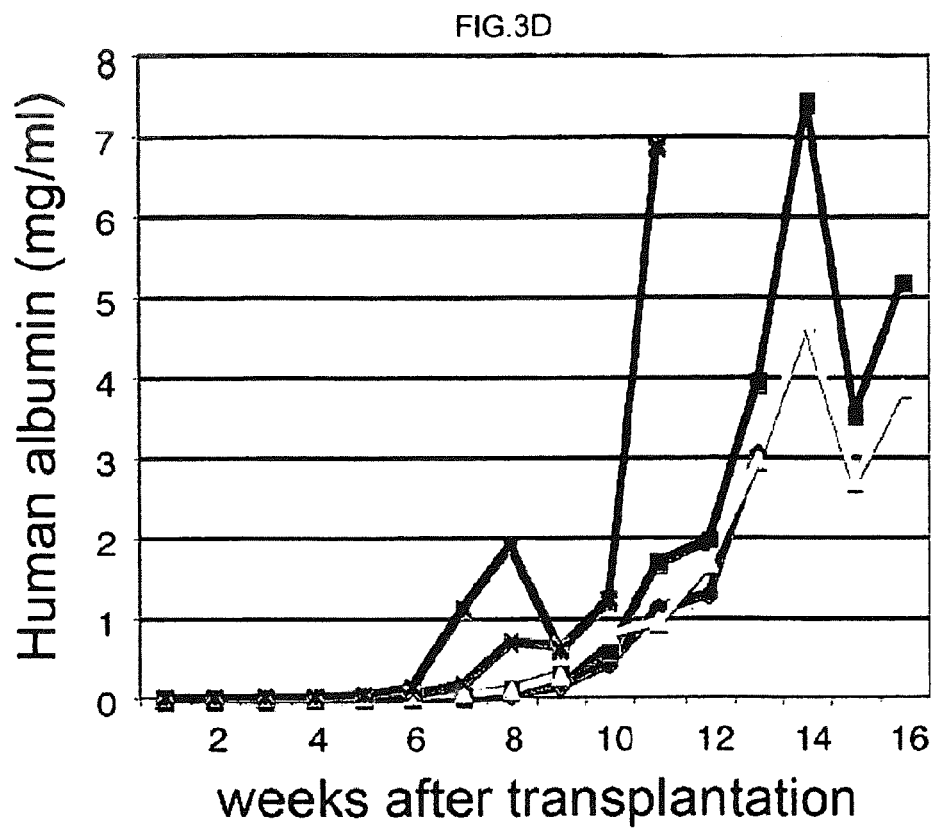
FIG. 3d (normal plotting) and FIG. 3e (logarithmic plotting) are graphs showing human albumin concentration of secondary recipients. Logarithmic plotting shows the doubling time of albumin concentration is approximately one week.

To examine whether repopulated human hepatocytes expressed mature hepatocyte-specific genes, RT-PCR was performed on messenger RNA extracted from recipient livers. The human albumin (ALB), FAH, transferrin (TF), transthyretin (TTR), tyrosine aminotransferase (TAT), and UGT1A1 genes were abundantly expressed in recipient livers (FIG. 3a, FIG. 6c and FIG. 7). Hepatocyte functionality was also assessed by measuring blood concentration of human albumin. An ELISA kit specific for human albumin was used, and the threshold for detection was 0.05 µg/ml using samples diluted 1:100. Human albumin was first detected at 4 to 10 weeks after transplantation in primary recipients. Although initially there was some fluctuation in levels, concentrations then increased relatively steadily for several more weeks (FIGS. 3b and FIG. 3c).

A pharmacological proteinase inhibitor may be necessary to keep highly repopulated mice viable long term; human complement produced by the donor hepatocytes could injure recipient kidney (see Tateno et al. *Am. J. Pathol.* 165:901-912, 2004). Therefore, several (n=3) highly repopulated mice were observed for an extended period. These mice did not lose weight while off NTBC for 4 months and their human albumin concentration remained stable. Furthermore, their kidneys were macroscopically and histologically normal at harvest (FIG. 2g).

Example 5

Serial Transplantation of Human Hepatocytes

One of the limitations of previously described liver xenorepopulation models is the inability to further expand engrafted human hepatocytes. In order to test the feasibility of serial transplantation in the FRG mouse system, the liver of a highly repopulated primary recipient (~70% human cells) was perfused, and parenchymal hepatocytes were collected using a standard collagenase digestion protocol.

Mice repopulated with human cells were anesthetized and portal vein or inferior vena cava was cannulated with a 24 gauge catheter. The liver was perfused with calcium- and magnesium-free EBSS supplemented with 0.5 mM EGTA and 10mM HEPES for 5 minutes. The solution was changed to EBSS supplemented with 0.1 mg/ml collagenase XI (sigma) and 0.05 mg/ml DNase I (sigma) for 10 minutes. The liver was gently minced in the second solution and filtered through 70 µm and 40 µm nylon mesh sequentially. After 150×g centrifugation for 5 minutes, the pellet was further washed twice at 50×g for 2 minutes. The number and viability of cells were assessed by the trypan blue exclusion test.

Figure 3E:
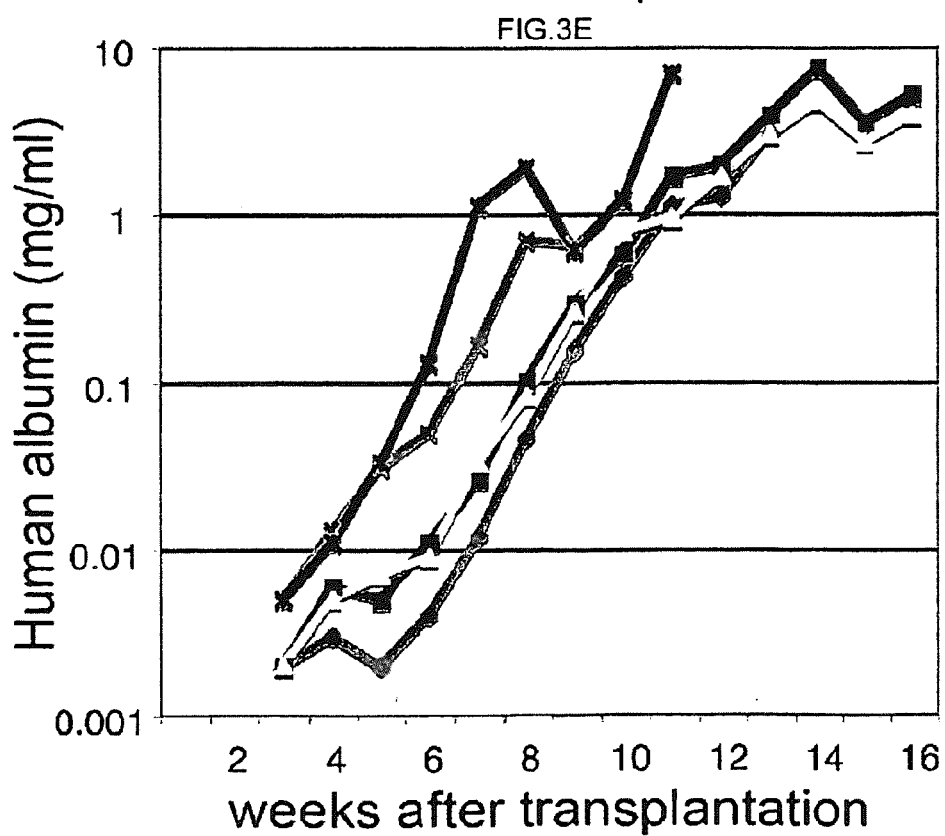
FIG. 3b (normal plotting) and FIG. 3c (logarithmic plotting) are graphs showing blood human albumin concentration of primary hepatocyte recipients using ELISA. The threshold concentration of the system is approximately 0.005 µg/ml.
Figure 4E:
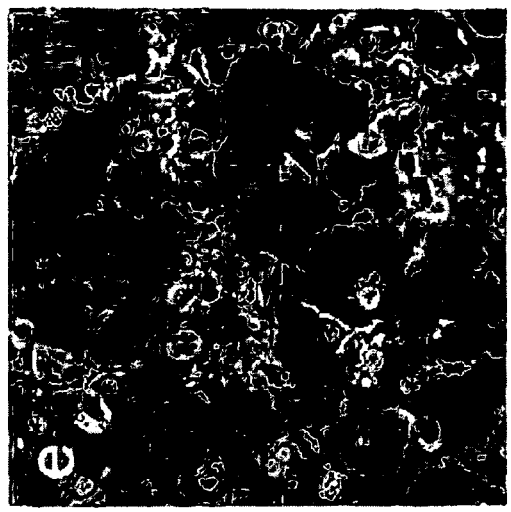
FIGS. 4c-e are digital images of hepatocytes analyzed by FAH immunocytochemistry demonstrating that more than 70% of cultured hepatocytes from a tertiary mouse were positive for FAH.
Figure 4D:
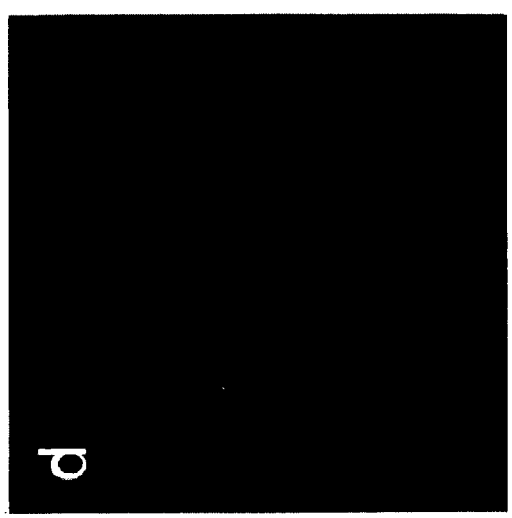
Figure 4C:
Figure 4F:
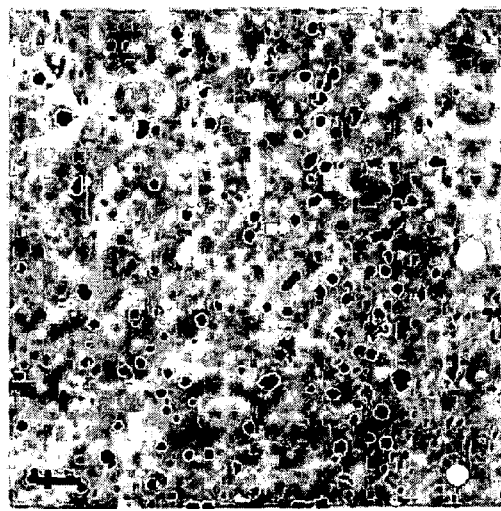
FIGS. 4f-h are digital images of tissue sections showing FAH immunohistochemistry of serially transplanted mice liver. Primary (FIG. 4f), secondary (FIG. 4g) and tertiary (FIG. 4h) recipient livers were repopulated by human hepatocytes.
Figure 4G:
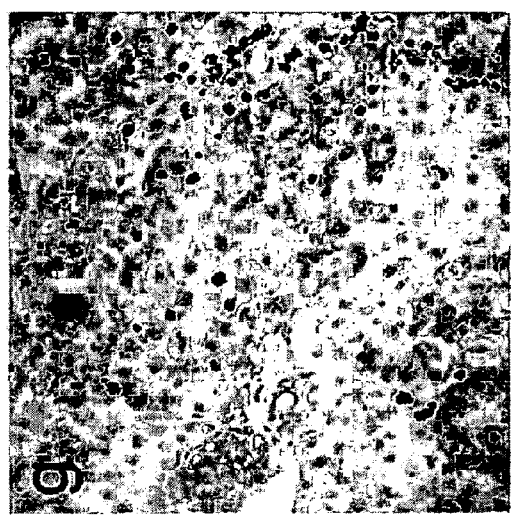
Figure 4H:

One million viable cells suspended in 100 µl DMEM were injected into recipient spleen via 27 gauge needle. Transplantation of hepatocytes into secondary FRG recipients was performed without separating the Fah-positive human and Fah-negative mouse hepatocytes. In contrast to the cells used for primary engraftment, the viability of human hepatocytes harvested in this fashion was >80%, and they readily attached to collagen-coated culture plates (FIGS. 4c-e). After engraftment of the secondary recipient, the serial transplantation was continued in a similar fashion into tertiary and quarternary recipients. In each generation, blood human albumin of some, but not all, recipient mice became highly positive (FIG. 4a). The percentage of highly repopulated mice was higher in serial transplant recipients (17/28 compared with 7/43) and the rate of albumin increase was more consistent (FIG. 3e). This may indicate that serial passage of hepatocytes enriches for the most transplantable human hepatocytes or it may simply reflect the higher quality and viability of cells harvested freshly from a donor mouse. Genomic PCR of the liver samples from albumin positive mice showed the presence of human DNA in each generation (FIG. 4b). Liver repopulation by human hepatocytes was also confirmed by fluorescent immunostaining against FAH (FIGS. 4c-e). Histological examination showed engrafted human hepatocytes were morphologically similar in each generation and were distinctly FAH-positive (FIGS. 4f-h).

Example 6

Hepatocyte Repopulation Is Not A Result of Cell Fusion

Figure 5C:
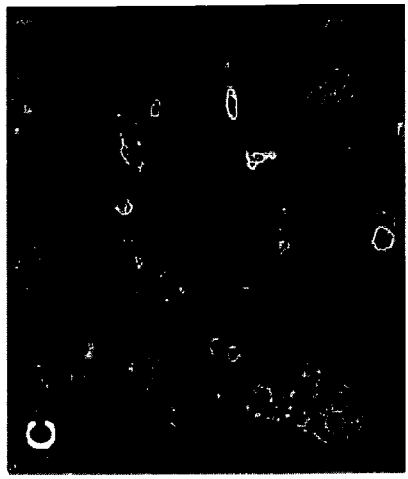
FIGS. 5a-c are digital images of anti-mouse albumin and anti-FAH immunocytochemistry of chimeric mouse hepatocytes. Most hepatocytes from chimeric liver were mouse albumin or FAH single positive.
Figure 5F:
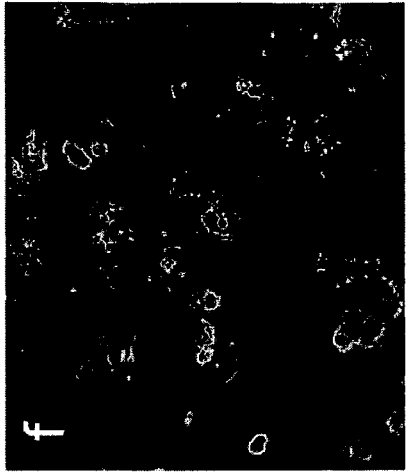
FIGS. 5d-f are digital images of anti-human albumin and anti-FAH immunocytochemistry of chimeric mouse hepatocytes. Most hepatocytes were human albumin and FAH double positive. Original magnification ×100.
Figure 5B:
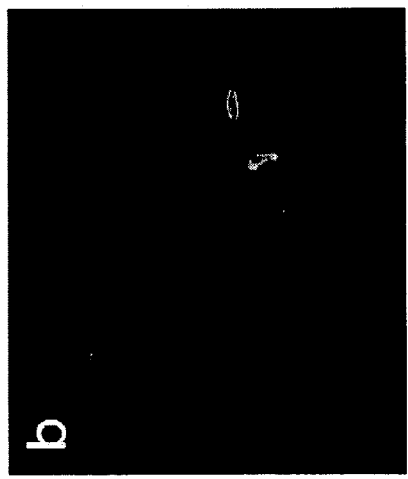
Figure 5E:
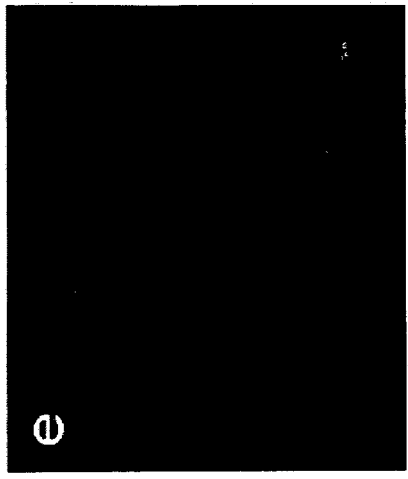
Figure 5A:
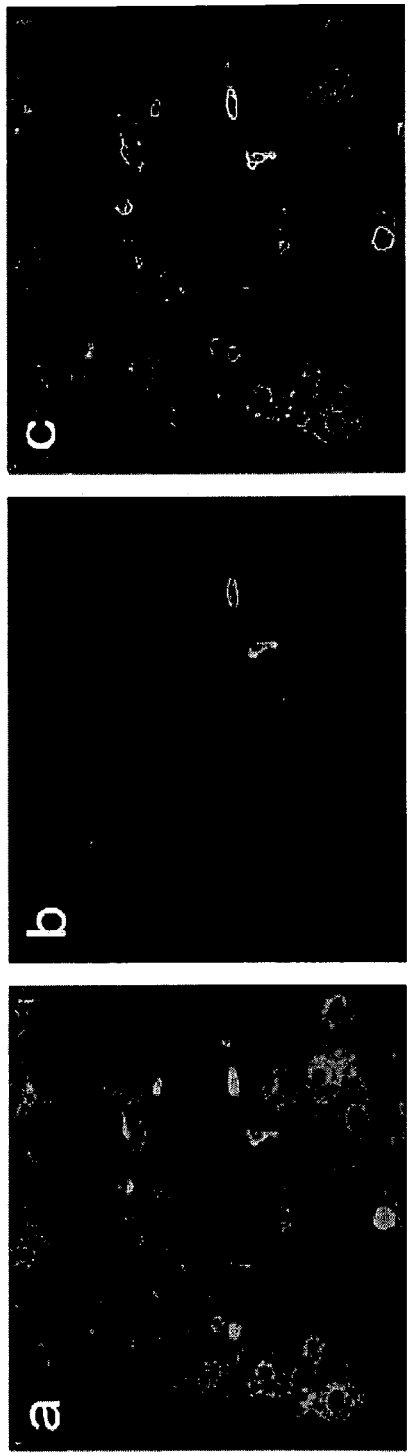
Figure 5D:
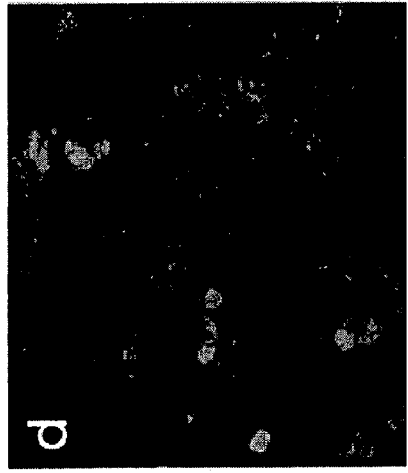

A recent report of liver repopulation with primate cells in urokinase transgenic mice demonstrated that cell fusion could potentially account for apparent "hepatocyte repopulation" (Okamura et al. *Histochem. Cell Biol.* 125:247-257, 2006). Since uPA-transgenic mice were used in that study, these findings raised the possibility that cell fusion was also the mechanism in other reports of mouse liver humanization. Cell fusion between hematopoietic cells and hepatocytes has also been observed in the Fah-deficient mice (Wang et al. *Nature* 422:897-901, 2003). Cell fusion between mouse and human cells would greatly diminish the value of humanized mouse livers for pharmaceutical applications. To confirm that the repopulated hepatocytes were truly human in origin, double immunostaining against human- or mouse-specific albumin and FAH was performed. Most (>95%) mouse albumin-positive hepatocytes were indeed negative for FAH and most FAH-positive hepatocytes were negative for mouse albumin (FIGS. 5a-c). On the other hand, almost all (>90%) human albumin-positive hepatocytes were also FAH-positive, while the remaining hepatocytes were double-negative (FIGS. 5d-f).

Figure 5L:
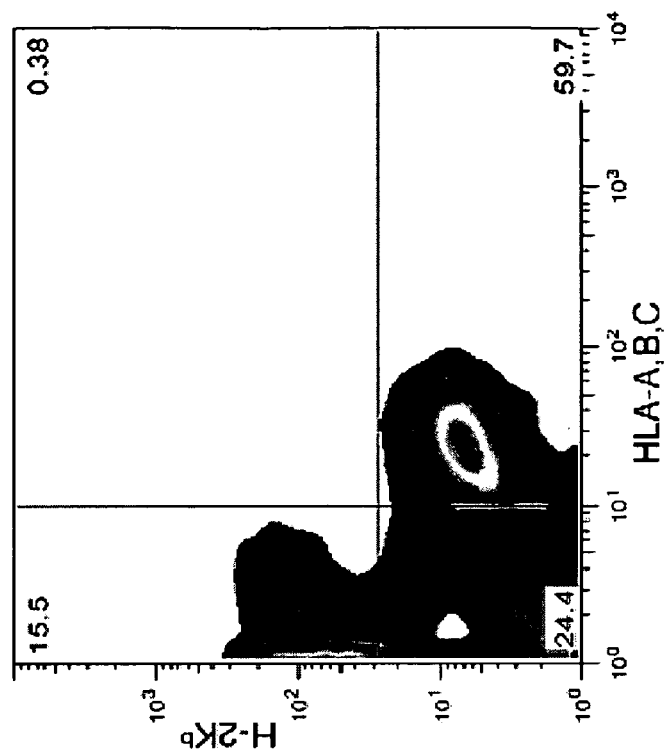
Figure 5K:
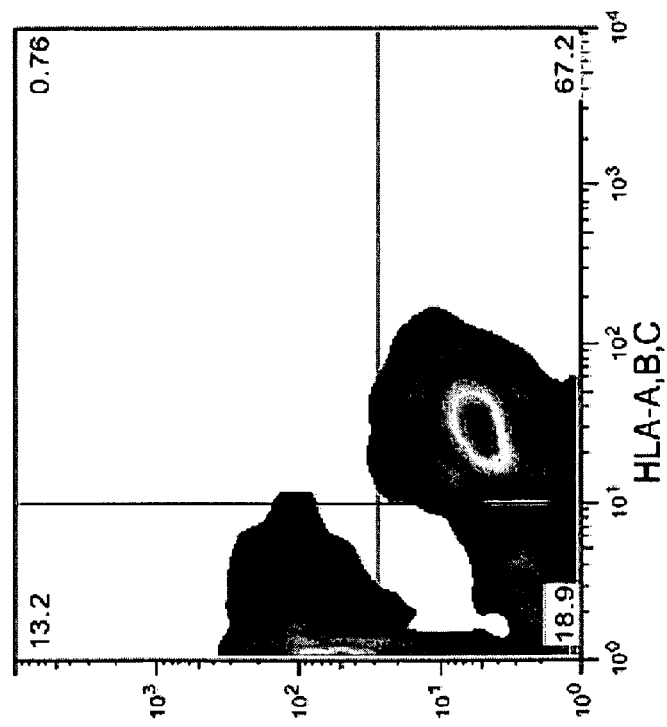
Figure 7A:
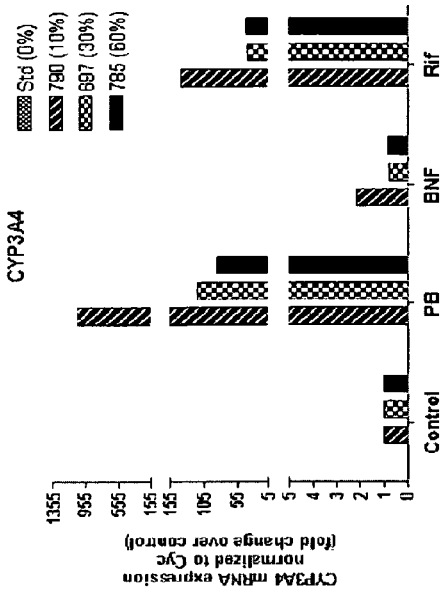
FIGS. 7a-h are graphs depicting basal gene expression levels of liver-specific genes and genes involved with drug metabolism in hepatocytes from three mice with different levels of human hepatocyte repopulation (M790 10%; M697 30%; and M785 60%).
Figure 7B:
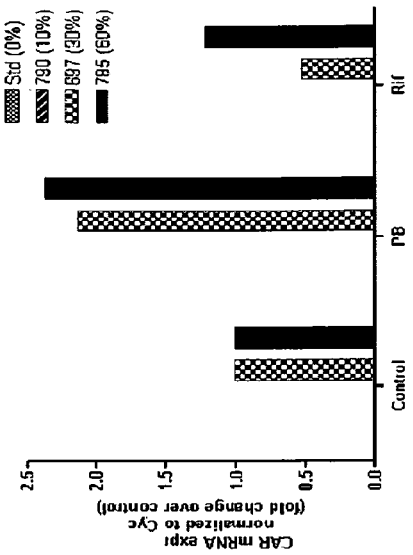
Figure 7C:
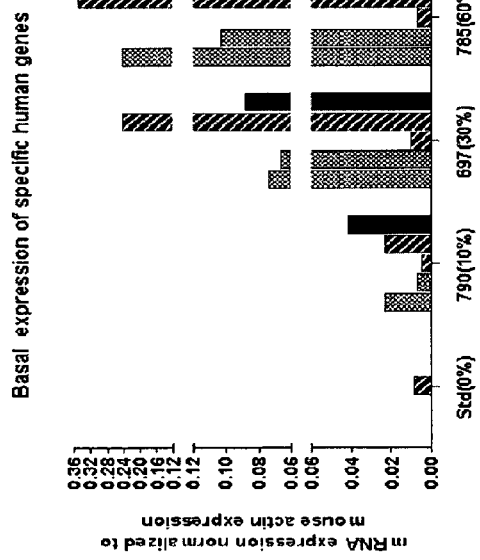
Figure 7D:
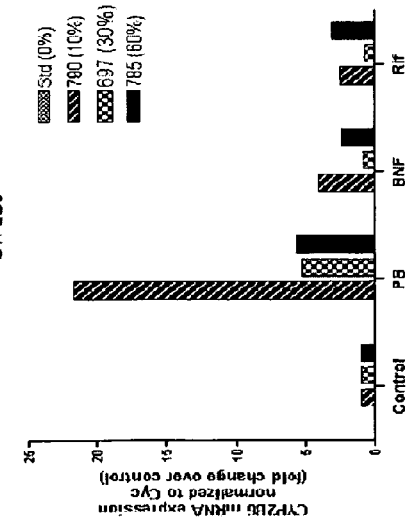
Figure 7F:
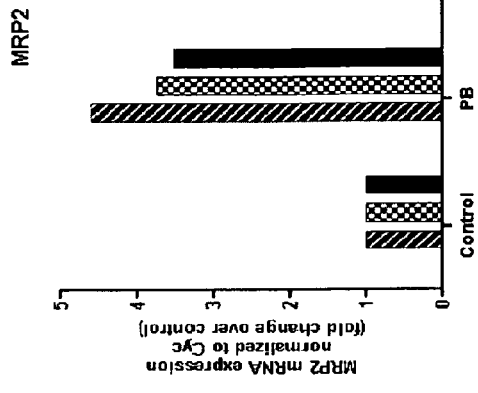
Figure 7H:
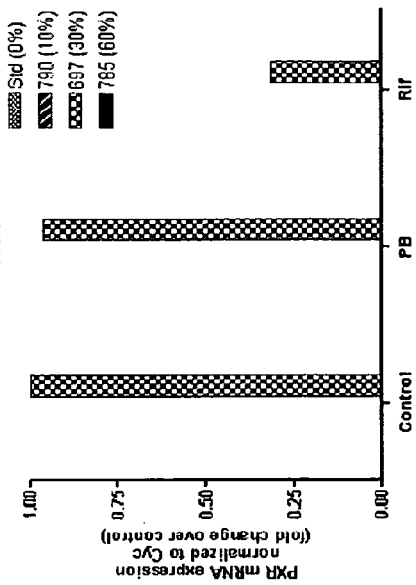
Figure 7E:
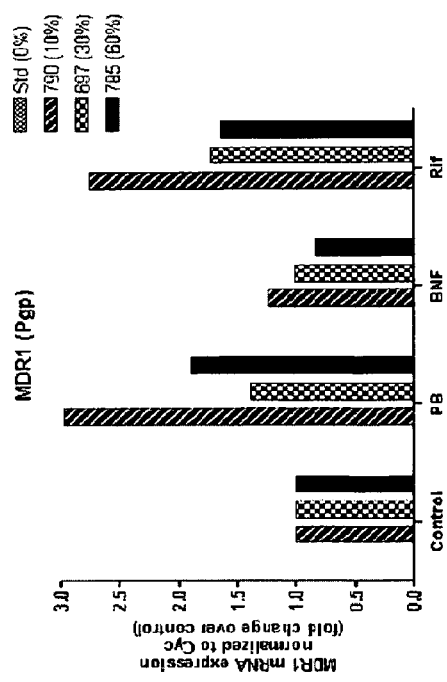
Figure 7G:
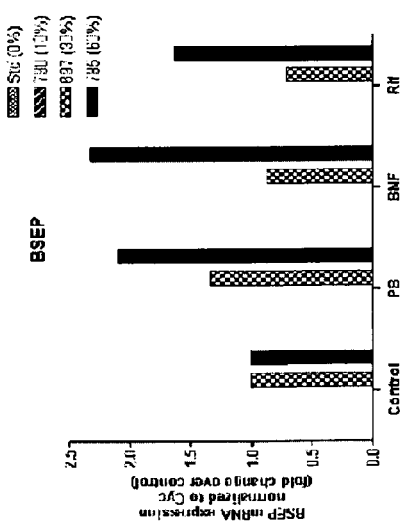

Albumin is a secreted protein and thus cells could appear antibody positive by taking up heterologous albumin from other cells. To further confirm the lack of cell fusion, human and mouse anti-major histocompatibility complex (MHC) antibodies were used for flow cytometry. Each antibody was confirmed to be species-specific (FIGS. 5g-j). No hepatocytes positive for the surface markers of both species were found in highly repopulated livers (FIG. 5k and FIG. 5l).

Finally, fluorescent in situ hybridization (FISH) was performed with human and mouse whole genome probes on hepatocytes from highly repopulated transplant recipients. Hepatocytes from highly repopulated primary (chimeric mouse #531) and tertiary (chimeric mouse #631) mice were hybridized with either human or mouse total genomic DNA. The percentage of cells positive for the human probe or the murine probe was scored (Table 3). Controls were pure human and mouse hepatocytes or an equal mix of human and mouse hepatocytes. If the human cells found in chimeric livers were the product of cell fusion, many hepatocytes would be double-positive for both human and mouse probes and hence the percentages of cells positive for mouse and human DNA would exceed 100%. Instead, the sum of the percentages closely approximated 100% as it did in the mix of human and murine hepatocytes. Furthermore, human hepatocytes were detected in the spleens of highly repopulated mice (FIG. 2h) despite the fact that the spleen is devoid of murine hepatocytes which could serve as fusion partners for human cells. Thus, double-positive cells (fusion products) could not account for the majority of human cells.

TABLE 3

Detection of human and mouse DNA in repopulated hepatocytes

|  | Mouse probe positive (%) | Human probe positive (%) | Sum of percentages |
|---|---|---|---|
| Murine hepatocytes | 87/87 (100) | 0/103 (0) | 100 |
| Human hepatocytes | 0/99 (0) | 107/107 (100) | 100 |
| Mix | 38/101 (38) | 68/115 (59) | 97 |
| Chimeric mouse #531 | 15/100 (15) | 95/111 (86) | 101 |
| Chimeric mouse #631 | 23/87 (26) | 69/94 (73) | 99 |

Taken together, these results indicate that fusion events, if they occurred, were rare and that the majority of repopulating cells were of purely human origin even when serial transplantation was performed. Therefore, human hepatocytes expanded in FRG mice have only human genetic and biochemical properties.

Example 7

Functional Characterization of Drug Metabolism in Humanized Mice

The basal expression and induction of human liver specific genes in chimeric mice was examined. Evaluation of testosterone metabolism and ethoxyresorufin-O-deethylase (EROD) activity on cultured hepatocytes was conducted as described by Kostrubsky et al. (*Drug Metab. Dispos.* 27:887-894, 1999), and Wen et al., (*Drug Metab. Dispos.* 30:977-984, 2002), respectively. RNA isolation, cDNA synthesis and real-time PCR were conducted as described by Komoroski et al., (*Drug Metab. Dispos.* 32:512-518, 2004). Primers, obtained from Applied Biosystems, were specific for human CYP1A1 (Hs00153120_m1), CYP1A2 (Hs00167927_m1), CYP3A4 (Hs00430021_m1), CYP3A7 (Hs00426361_a1), CYP2B6 (Hs00167937_g1), CYP2D6 (Hs00164385_a1), Multidrug resistance associated protein MRP2 (Hs00166123_m1), Bile Salt export Pump BSEP, (Hs00184829_m1), CAR (Hs00231959_m1) Albumin (Hs00609411_m1), HNF4α

(Hs00230853_m1), Cyclophillin (Hs99999904_m1) and mouse actin (Ma00607939_s1).

Cultures of isolated hepatocytes were established and exposed to prototypical inducers of the cytochrome P450 genes. The results demonstrated that the basal gene expression levels of cytochrome (CYP1A1, CYP1A2, CYP2B6, CYP3A4, CYP3A7), transporter (BSEP, MRP2) and drug conjugating enzymes (UGT1A1) were exactly those found in cultured normal adult human hepatocytes (FIG. 6c, FIG. 7). Furthermore, the pattern of genes induced by compounds such as beta-naphthoflavone (BNF), phenobarbital (PB) and rifampicin (Rif) was as expected from normal human cells. In addition to the mRNA expression levels of human drug metabolism genes, the enzymatic activity of the human CYP1A and 3A family members were measured. Ethoxyresorufin-O-deethylase activity (EROD) is known to be mediated by CYP1A1 and 1A2 in human liver. The results show that EROD activity was specifically and robustly induced by prior exposure to BNF in humanized mouse liver cells (FIG. 6a). Conversely, prior exposure to PB or rifampicin specifically induced the conversion of testosterone to 6-beta-hydroxyltestosterone, a specific measurement of CYP3A4 mediated metabolism (FIG. 6b). Thus, hepatocytes from repopulated FRG livers were indistinguishable from normal human adult hepatocytes in these standard drug metabolism assays.

Example 8

Depletion of Macrophages Prior to Hepatocyte Repopulation

Primary engraftment did not occur in 100% of FRG recipient mice, even with urokinase adenovirus pre-administration. It is possible that hepatic macrophages, which are present in normal numbers in FRG mice, limit human cell engraftment by promoting an innate immune response.

To eliminate a potential macrophage-initiated immune response, FRG mice are depleted of macrophages prior to human hepatocyte transplantation. Macrophage depletion can be achieved using any one of a number of methods well known in the art, including chemical depletion (Schiedner et al. *Mol. Ther.* 7:35-43, 2003) or by using antibodies (McKenzie et al. *Blood* 106:1259-1261, 2005). Macrophages also can be deleted using clodronate-containing liposomes (van Rijn et al. *Blood* 102:2522-2531, 2003). Additional compounds and compositions for depleting macrophages are described in U.S. Pat. Publication No. 2004-0141967 and PCT Publication No. WO 02/087424, which are herein incorporated by reference. Following macrophage depletion, FRG mice are transplanted, or serially transplanted, with human hepatocytes according to the methods described in the previous Examples herein.

Example 9

Engraftment of Human Hepatocytes in $F^{pm}$RG Mice

FRG mice contain a deletion in exon 5 of the Fah gene (Fah$^{\Delta exon5}$). To confirm that human hepatocytes can be engrafted and expanded in other models of Fah deficiency, a mouse strain containing a point mutation in Fah was generated. These mice, called Fah point mutation (Fah$^{pm}$) mice, have a point mutation in the Fah gene that causes missplicing and loss of exon 7 in the Fah mRNA (Aponte et al., *Proc. Natl. Acad. Sci. USA* 98:641-645, 2001, herein incorporated by reference). No differences in phenotype were detected between Fah$^{pm}$ mice and Fah$^{\Delta exon5}$ mice.

Fah$^{pm}$ mice were crossed with Rag2$^{-/-}$/Il2rg$^{-/-}$ mice (as described in Example 1) to produce homozygous Fah$^{pm}$/Rag2$^{-/-}$Il2rg$^{-/-}$ (F$^{pm}$RG) triple mutant mice. Two cohorts of F$^{pm}$RG mice were transplanted with human hepatocytes according to the methods described in Example 4. Approximately 24-48 hours prior to hepatocyte transplantation, mice received an intravenous injection (retroorbital) of uPA adenovirus. For comparison, FRG mice were transplanted with human hepatocytes in parallel. Human serum albumin was detected in the peripheral blood of F$^{pm}$RG mice at highly significant levels (23 µg/ml) two and three months after transplantation. These blood levels of human serum albumin were similar to levels found in FRG mice transplanted at the same time.

These results indicate that F$^{pm}$RG mice can be repopulated with human hepatocytes to the same extent as FRG mice. Therefore, humanized liver repopulation is not unique to FRG mice with the Fah$^{\Delta exon5}$ mutation, but can be achieved with any strain of Fah deficient mice.

This disclosure provides a method for in vivo expansion of human hepatocytes. The disclosure further provides a genetically modified, immunodeficient mouse useful for expanding human hepatocytes in vivo. It will be apparent that the precise details of the methods described may be varied or modified without departing from the spirit of the described invention. We claim all such modifications and variations that fall within the scope and spirit of the claims below.

The invention claimed is:

1. A method of expanding human hepatocytes in vivo, comprising:
   i) transplanting human hepatocytes into a Rag2$^{-/-}$/Il2rg$^{-/-}$ mouse, wherein the mouse is deficient for expression of Fah; and
   ii) allowing the human hepatocytes to expand for at least about two weeks, thereby expanding the human hepatocytes.

2. The method of claim 1, wherein the mouse is a Fah$^{-/-}$/Rag2$^{-/-}$/Il2rg$^{-/-}$ (FRG) mouse.

3. The method of claim 1, wherein the mouse is a Fah$^{pm}$/Rag2$^{-/-}$/Il2rg$^{-/-}$ (F$^{pm}$RG) mouse.

4. The method of claim 1, wherein a vector encoding human urokinase is administered to the mouse prior to transplanting the human hepatocytes.

5. The method of claim 4, wherein the urokinase is a secreted form of urokinase.

6. The method of claim 4, wherein the urokinase is a non-secreted form of urokinase.

7. The method of claim 1, wherein the mouse is administered 2-(2-nitro-4-trifluoro-methyl-benzoyl)-1,3 cyclohexanedione (NTBC) prior to hepatocyte transplantation.

8. The method of claim 7, wherein the NTBC is administered at a dose of about 0.05 mg/kg/day to about 0.10 mg/kg/day.

9. The method of claim 1, wherein transplanting the human hepatocytes comprises injecting the human hepatocytes into the spleen or portal vein of the mouse.

10. The method of claim 1, wherein the transplanted human hepatocytes were isolated from the liver of an organ donor, isolated from a surgical resection, or derived from a stem cell, monocyte or amniocyte.

11. The method of claim 1, wherein the transplanted human hepatocytes were cryopreserved prior to transplantation.

12. The method of claim 2, further comprising depleting macrophages from the FRG mouse prior to hepatocyte transplantation.

13. A genetically modified mouse whose genome is homozygous for deletions or one or more point mutations in the Fah, Rag2 and Il2rg genes such that the deletions or point mutations result in loss of expression of functional FAH, RAG-2 and IL-2Rγproteins, wherein the mouse is immunodeficient and exhibits decreased liver function, and wherein human hepatocytes can be expanded in the mouse.

14. The mouse of claim 13, wherein the deletions or point mutations result in the complete loss of B cells, T cells and NK cells in the mouse.

15. The mouse of claim 13, wherein the mouse is a FRG mouse.

16. The mouse of claim 13, wherein the mouse is a F$^{pm}$RG mouse.

17. The mouse of claim 13, wherein the mouse expresses human urokinase.

18. The mouse of claim 17, wherein the urokinase is a secreted form of urokinase.

19. The mouse of claim 17, wherein the urokinase is a non-secreted form of urokinase.

20. The mouse of claim 17, wherein expression of human urokinase results from incorporation of a transgene encoding human urokinase into the genome of the mouse.

21. The mouse of claim 17, wherein expression of human urokinase results from administration of a vector encoding human urokinase.

22. The method of claim 1, wherein the human hepatocytes are isolated human hepatocytes.

23. The method of claim 1, further comprising collecting human hepatocytes from the mouse.

24. The method of claim 23, wherein the human hepatocytes are collected from the liver of the mouse.

25. The method of claim 23, further comprising expanding the collected human hepatocytes by serial transplantation.

26. The method of claim 1, further comprising collecting a biological sample from the mouse.

27. The method of claim 26, wherein the biological sample is a blood, urine, cell or tissue sample.

* * * * *